(12) United States Patent
Tertel et al.

(10) Patent No.: US 11,492,306 B2
(45) Date of Patent: Nov. 8, 2022

(54) ALKYLATION PROCESS WITH THERMAL OXIDATION SYSTEM

(71) Applicant: HONEYWELL INTERNATIONAL INC., Charlotte, NC (US)

(72) Inventors: Jonathan A. Tertel, Mount Prospect, IL (US); Rajeswar R. Gattupalli, Buffalo Grove, IL (US); Jan De Ren, Bracknell (GB); William J. Whyman, Tulsa, OK (US); David A. Roman, Surrey (GB)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 17/361,674

(22) Filed: Jun. 29, 2021

(65) Prior Publication Data
US 2022/0098129 A1 Mar. 31, 2022

Related U.S. Application Data

(60) Provisional application No. 63/085,250, filed on Sep. 30, 2020.

(51) Int. Cl.
*C07C 2/62* (2006.01)
*C07C 7/12* (2006.01)
*C07C 7/00* (2006.01)
*C07C 2/70* (2006.01)

(52) U.S. Cl.
CPC .................. *C07C 2/62* (2013.01); *C07C 2/70* (2013.01); *C07C 7/005* (2013.01); *C07C 7/12* (2013.01)

(58) Field of Classification Search
CPC .. C07C 2/62; C07C 2/70; C07C 7/005; C07C 7/12
See application file for complete search history.

(56) References Cited

U.S. PATENT DOCUMENTS

| | | | | |
|---|---|---|---|---|
| 2,966,530 | A | * 12/1960 | Quinlan | .................... C07C 2/70 75/670 |
| 3,567,433 | A | 3/1971 | Gutnikov | |
| 3,721,720 | A | * 3/1973 | Chapman et al. | ........ C07C 2/62 585/723 |

(Continued)

FOREIGN PATENT DOCUMENTS

| CA | 2706957 A1 | 6/2009 |
|---|---|---|
| CN | 101239758 A | 8/2008 |

(Continued)

OTHER PUBLICATIONS

Nafis, Douglas A. et al., Alkylation in Petroleum Processing, In: Treese, S., Jones, D., Pujado P., Handbook of Petroleum Processing, Springer, Cham. https://doi.org/10.1007/978-3-319-05545-9_5-1, Jan. 29, 2015.

(Continued)

*Primary Examiner* — Ali Z Fadhel

(57) ABSTRACT

Processes for treating effluent streams in alkylation processes are described. One or more process streams rom HF alkylation processes, $H_2SO_4$ alkylation processes, or ionic liquid alkylation processes can be thermally oxidized in a thermal oxidation system. The thermal oxidation system can replace at least one of the caustic wash unit, the neutralization unit, and the acid gas treatment unit.

20 Claims, 4 Drawing Sheets

(56) References Cited

U.S. PATENT DOCUMENTS

| | | | |
|---|---|---|---|
| 4,014,982 A * | 3/1977 | Paull | C01B 17/34 |
| | | | 423/523 |
| 4,376,107 A * | 3/1983 | Morgenthaler | C01B 17/745 |
| | | | 423/528 |
| 4,377,470 A | 3/1983 | Hettinger, Jr. et al. | |
| 4,430,517 A | 2/1984 | Imai et al. | |
| 4,479,926 A * | 10/1984 | Behrmann | C01F 11/22 |
| | | | 423/467 |
| 4,514,368 A | 4/1985 | Hubred | |
| 4,544,533 A | 10/1985 | Marcantonio | |
| 4,762,812 A | 8/1988 | Lopez et al. | |
| 5,098,668 A | 3/1992 | Callen et al. | |
| 5,336,832 A * | 8/1994 | Keller | C07C 2/62 |
| | | | 585/710 |
| 5,339,755 A | 8/1994 | Smith | |
| 5,365,010 A | 11/1994 | Rao et al. | |
| 6,449,954 B2 | 9/2002 | Bachmann | |
| 6,514,904 B1 | 2/2003 | Moser et al. | |
| 7,002,048 B2 | 2/2006 | Wijesekera et al. | |
| 7,034,192 B2 | 4/2006 | Wijesekera | |
| 7,126,029 B2 | 10/2006 | Skipworth et al. | |
| 7,141,700 B1 | 11/2006 | Schmidt et al. | |
| 7,141,701 B1 | 11/2006 | Schmidt et al. | |
| 7,166,752 B2 | 1/2007 | Marshall, Jr. et al. | |
| 7,186,866 B1 | 3/2007 | Keenan et al. | |
| 7,417,003 B2 | 8/2008 | Schmidt et al. | |
| 7,674,739 B2 | 3/2010 | Elomari et al. | |
| 7,652,181 B1 | 4/2010 | Schmidt et al. | |
| 7,700,511 B2 | 4/2010 | Reynolds et al. | |
| 7,740,751 B2 | 6/2010 | Peters | |
| 7,744,828 B2 | 6/2010 | Schmidt et al. | |
| 7,841,807 B2 | 11/2010 | Naunheimer et al. | |
| 7,878,736 B2 | 2/2011 | Naunheimer et al. | |
| 7,888,537 B2 | 2/2011 | Schmidt et al. | |
| 8,242,320 B2 | 8/2012 | Schmidt et al. | |
| 8,329,603 B2 | 12/2012 | Randolph et al. | |
| 8,387,645 B2 | 3/2013 | Shafe | |
| 8,457,278 B2 | 6/2013 | Fadler | |
| 8,518,847 B2 | 8/2013 | Jan et al. | |
| 8,608,941 B2 | 12/2013 | Haizmann et al. | |
| 8,609,915 B2 | 12/2013 | Majumdere et al. | |
| 8,609,916 B2 | 12/2013 | Majumder et al. | |
| 8,679,321 B2 | 3/2014 | Negiz et al. | |
| 8,853,481 B2 | 10/2014 | Jan et al. | |
| 9,006,123 B2 | 4/2015 | Nabozny | |
| 9,079,816 B2 | 7/2015 | Johnson et al. | |
| 9,138,738 B1 | 9/2015 | Glover et al. | |
| 9,150,469 B2 | 10/2015 | Bullen et al. | |
| 9,181,150 B1 | 11/2015 | Smith et al. | |
| 9,206,362 B2 | 12/2015 | Haizmann et al. | |
| 9,290,826 B2 | 3/2016 | Da Costa et al. | |
| 9,302,951 B2 | 4/2016 | Stevens et al. | |
| 9,321,783 B2 | 4/2016 | Ibert et al. | |
| 9,327,259 B2 | 5/2016 | Hartman et al. | |
| 9,328,037 B2 | 5/2016 | Riley et al. | |
| 9,359,917 B2 | 6/2016 | Koseoglu et al. | |
| 9,360,252 B2 | 6/2016 | Furlong et al. | |
| 9,399,604 B2 | 7/2016 | Martins et al. | |
| 9,416,321 B2 | 8/2016 | Eizenga et al. | |
| 9,469,818 B2 | 10/2016 | Baldriaghi et al. | |
| 9,523,050 B2 | 12/2016 | Pandranki et al. | |
| 9,567,264 B2 | 2/2017 | Fichtl | |
| 9,637,699 B2 | 5/2017 | Ellig et al. | |
| 9,718,047 B2 | 8/2017 | Moser et al. | |
| 9,745,523 B2 | 8/2017 | Ganguly et al. | |
| 9,815,756 B2 | 11/2017 | Schmidt et al. | |
| 9,822,314 B2 | 11/2017 | Ray | |
| 9,914,675 B2 | 3/2018 | Buchbinder et al. | |
| 9,914,880 B2 | 3/2018 | Fichtl et al. | |
| 9,914,883 B2 | 3/2018 | Dutta et al. | |
| 10,041,004 B2 | 8/2018 | Govindhakannan et al. | |
| 10,240,099 B2 | 3/2019 | Mani et al. | |
| 10,384,186 B2 | 8/2019 | Egolf et al. | |
| 10,399,852 B2 | 9/2019 | De Ren et al. | |
| 10,429,066 B2 | 10/2019 | Schroter et al. | |
| 10,577,539 B2 | 3/2020 | Brodeur-Campbell et al. | |
| 10,577,547 B2 | 3/2020 | Wexler et al. | |
| 2008/0033227 A1 * | 2/2008 | Graves | C07C 2/62 |
| | | | 585/707 |
| 2008/0207971 A1 | 8/2008 | Gray et al. | |
| 2008/0308503 A1 * | 12/2008 | Zhang | C10G 33/06 |
| | | | 210/799 |
| 2009/0226353 A1 * | 9/2009 | Tekie | C01B 17/508 |
| | | | 423/220 |
| 2009/0226364 A1 * | 9/2009 | Tekie | C01B 17/508 |
| | | | 423/576.8 |
| 2012/0058545 A1 * | 3/2012 | Schreuder | B01D 53/1456 |
| | | | 435/294.1 |
| 2013/0087481 A1 | 4/2013 | Heraud et al. | |
| 2015/0094486 A1 | 4/2015 | Buchbinder et al. | |
| 2015/0119232 A1 * | 4/2015 | Moser | B01J 38/12 |
| | | | 422/187 |
| 2016/0168054 A1 | 6/2016 | Kalnes et al. | |
| 2017/0001893 A1 * | 1/2017 | Gurney | C02F 1/048 |
| 2017/0216827 A1 * | 8/2017 | Girgis | C07C 2/62 |
| 2019/0144766 A1 | 5/2019 | Yokomizo et al. | |
| 2019/0292949 A1 | 9/2019 | Sonnek et al. | |
| 2020/0222851 A1 | 7/2020 | De Ren et al. | |

FOREIGN PATENT DOCUMENTS

| | | | |
|---|---|---|---|
| EP | 0320094 A2 | 6/1989 | |
| EP | 1218890 A2 * | 7/2002 | G21C 19/48 |
| EP | 1218890 A2 | 7/2002 | |
| WO | 2020150353 A1 | 7/2020 | |

OTHER PUBLICATIONS

International Search Report from corresponding PCT application No. PCT/US2021/071072 dated Oct. 14, 2021.

Written Opinion from corresponding PCT application No. PCT/US2021/071072 dated Oct. 14, 2021.

Levy, Edward et al., Recovery of Water from Boiler Flue Gas Using Condensing Heat Exchangers, Final Technical Report issued Jun. 2011, Energy Research Center.

Liu, Xinpeng et al., Desulfurization and regeneration performance of heteropoly compound/ionic liquid solutions at high temperature, Chemical Engineering Journal 316, 2017, 171-178.

* cited by examiner

ALKYLATION PROCESS WITH THERMAL OXIDATION SYSTEM

RELATED APPLICATIONS

This application claims the benefit of U.S. Provisional Patent Application Ser. No. 63/085,250 filed Sep. 30, 2020, the entirety of which is incorporated herein by reference.

BACKGROUND

Alkylation is typically used to combine light olefins, for example mixtures of alkenes such as propylene and butene, with isobutane to produce a relatively high-octane branched-chain paraffinic hydrocarbon fuel, including isoheptane and isooctane. Similarly, an alkylation reaction can be performed using an aromatic compound such as benzene in place of the isobutane. When using benzene, the product resulting from the alkylation reaction is an alkylbenzene (e.g. ethylbenzene, cumene, dodecylbenzene, etc.).

The alkylation of paraffins with olefins for the production of alkylate for gasoline can use a variety of catalysts. The choice of catalyst depends on the end product a producer desires. Typical alkylation catalysts include liquid acid catalysts, such as hydrofluoric acid (HF), sulfuric acid ($H_2SO_4$), and acid ionic liquid catalysts. HF and $H_2SO_4$ alkylation processes generate large amounts of acidic waste including acid soluble oils (ASO) that must be treated and disposed of. Ionic liquids, although very stable, will react with oxygen in the feed, which requires removing the spent ionic liquid from the alkylation process.

Treatment of these acidic waste streams requires chemicals, as well as additional capital and operating costs for the caustic wash unit, the neutralization unit, and the acid gas treatment unit, as well as disposal costs. Moreover, these treatments may not be sufficient to meet increasingly stringent environmental regulations.

Therefore, there is a need for an improved process for treating effluent streams in alkylation processes.

DESCRIPTION OF THE INVENTION

Figure 1:
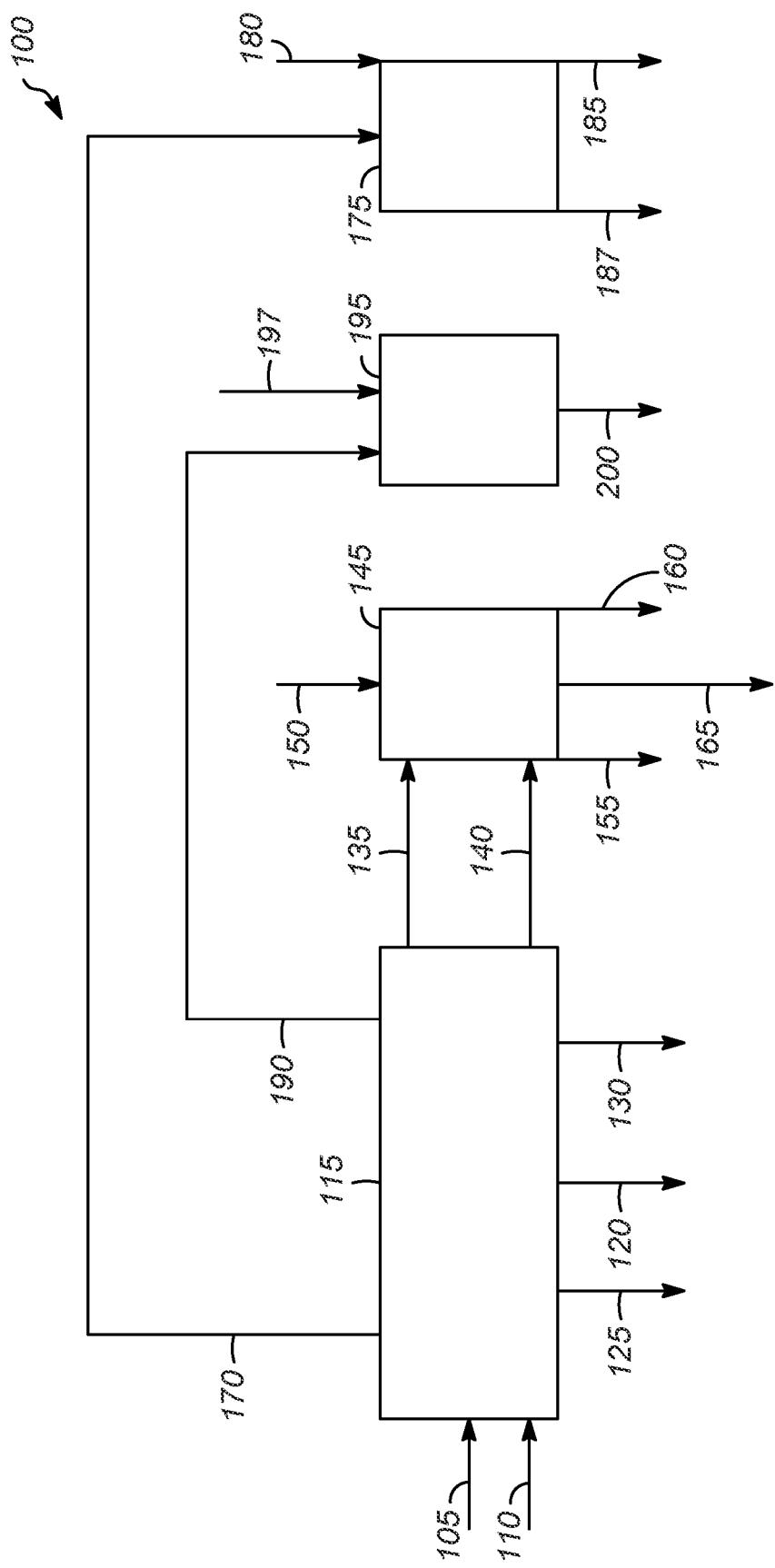
FIG. 1 is an illustration of one embodiment of an alkylation process.

The present invention relates to a process for treating effluent streams in alkylation processes. At least one of the caustic wash unit, the neutralization unit, and the acid gas treatment unit, can be replaced with a thermal oxidation system. The elimination of several process units with their associated equipment decreases the capital costs. The operating costs are reduced as a result of decreasing or eliminating the corrosion problems and environmental issues and chemical requirements and disposal of spent caustic streams, e.g., spent NaOH or KOH.

Additionally, energy costs are reduced as a result of optional waste heat recovery. Waste heat can be recovered in the form of steam, hot oil, electricity, or combinations thereof. The steam and/or hot oil and/or electricity can be used to supply heat requirements in various pieces of equipment in the alkylation process or elsewhere. This includes, but is not limited to, reboilers for a variety of columns such as an isostripper column, a depropanizer column, an HCL stripper column, a rerun column, and an HF stripper column.

One aspect of the invention is a process for treating off-gas and waste effluent streams in an alkylation complex. In one embodiment, the process comprises: thermally oxidizing at least one of: an acid soluble oil (acid ASO) stream from a liquid acid alkylation process section, an acid gas stream from the liquid acid alkylation process section, an acid liquid stream from the liquid acid alkylation process section, a neutralized ASO stream from a caustic wash zone, and a spent caustic stream from an acid gas scrubber zone; or an acid spent ionic liquid from an ionic liquid alkylation process section, an acid gas stream from the ionic liquid alkylation process section, an acid liquid stream from the ionic liquid alkylation process section, a neutralized spent ionic liquid from an ionic liquid caustic wash zone, and a spent caustic stream from an acid gas scrubber zone; in a thermal oxidation system, comprising; thermally oxidizing the at least one of: the acid ASO stream from the liquid acid alkylation process section, the acid gas stream from the liquid acid alkylation process section, the acid liquid stream from the liquid acid alkylation process section, the acid spent ionic liquid from the ionic liquid alkylation process section, the acid gas stream from the ionic liquid alkylation process section, the neutralized ASO stream from the caustic wash zone, and the spent caustic stream from the acid gas scrubber zone; or the acid liquid stream from the ionic liquid alkylation process section, the neutralized spent ionic liquid from the ionic liquid caustic wash zone, and the spent caustic stream from the acid gas scrubber zone, in a thermal oxidizing section forming flue gas consisting essentially of at least one of $H_2O$, $CO_2$, $N_2$, $O_2$, SOx, NOx, HCl, $Cl_2$, HF, $F_2$, $Na_2O$, $Na_2SO_3$, $Na_2SO_4$, $Na_2CO_3$, NaCl, NaF, $CaF_2$, CaO, $CaSO_3$, $CaSO_4$, $CaCO_3$, $CaCl_2$, $K_2O$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO; optionally recovering waste heat from the flue gas in a waste heat recovery section; removing at least one of SOx, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO from the flue gas in a contaminant removal section to form a decontaminated outlet flue gas consisting essentially of at least one of $H_2O$, $CO_2$, $N_2$, $O_2$, and NOx, wherein removing the at least one of SOx, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO from the flue gas comprises: quenching the flue gas in a quench section to form quenched flue gas after recovering the waste heat; and contacting a caustic solution with the quenched flue gas in a contaminant scrubbing section to form the decontaminated outlet flue gas and a liquid stream comprising at least one of $H_2O$, NaCl, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO; or reacting the flue gas with a reactant in a contaminant reaction section to form a reaction section flue gas consisting essentially of at least one of $H_2O$, $CO_2$, $N_2$, $O_2$, $Na_2SO_4$, $Na_2CO_3$, NaCl, NaF, $CaF_2$, $CaSO_4$, $CaCO_3$, $CaCl_2$, $K_2SO_4$, $K_2CO_3$, KCl, KF, $Al_2O_3$, NiO, FeO, $FeO_2$, $Fe_2O_3$, $Fe_3O_4$, and CuO wherein the reactant comprises at least one of $NaHCO_3$, $NaHCO_3 \cdot Na_2CO_3 \cdot 2(H_2O)$, $CaCO_3$ and $Ca(OH)_2$; and filtering the reaction section flue gas in a filtration section to remove at least one of $Na_2SO_4$, $Na_2CO_3$, NaCl, NaF, $CaF_2$, $CaSO_4$, $CaCO_3$, $CaCl_2$, $K_2SO_4$, $K_2CO_3$, KCl, KF, $Al_2O_3$, NiO, FeO, $FeO_2$, $Fe_2O_3$, $Fe_3O_4$, and CuO to form the decontaminated outlet flue gas; and optionally removing NOx from the decontaminated outlet flue gas in an NOx removal section to form a de-NOx outlet flue gas consisting essentially of at least one of $H_2O$, $CO_2$, $N_2$, and $O_2$.

In some embodiments, the liquid acid alkylation process section comprises an HF alkylation process section or an $H_2SO_4$ alkylation process section.

In some embodiments, the liquid acid alkylation process section comprises an HF alkylation process section, further comprising: alkylating a $C_{3-4}$ olefin stream comprising propylene and butene and an isobutane stream comprising isobutane in the HF alkylation process section in the presence of an acid catalyst comprising HF to produce a reaction mixture comprising alkylate, unreacted propylene, unreacted normal butene, HF catalyst, and spent HF catalyst; separating the reaction mixture into an alkylate stream, an HF catalyst stream, the acid ASO stream comprising spent HF catalyst, the acid gas stream, the acid liquid stream, and a stream comprising at least one of the unreacted propylene and the unreacted normal butene; thermally oxidizing at least one of the acid ASO stream, the acid gas stream, and the acid liquid stream.

In some embodiments, the process further comprises: neutralizing at least one of the acid ASO stream, the acid gas stream, the acid liquid stream with caustic forming at least one of the neutralized ASO stream, a neutralized gas stream, a neutralized liquid stream, and a spent caustic stream; thermally oxidizing at least one of the neutralized ASO stream, the neutralized gas stream, the neutralized liquid stream, and the spent caustic stream.

In some embodiments, the process further comprises: introducing at least one of the neutralized ASO stream into a neutralized ASO surge tank before thermally oxidizing the neutralized ASO stream and introducing the neutralized liquid stream into a neutralized liquid surge tank before thermally oxidizing the neutralized liquid stream.In some embodiments, the process further comprises: introducing and least one of the acid ASO stream into an acid ASO surge tank before thermally oxidizing the acid ASO stream and introducing the acid liquid stream into an acid liquid surge tank before thermally oxidizing the acid liquid stream.

In some embodiments, the alkylation process section comprises an $H_2SO_4$ alkylation process section, further comprising: alkylating a $C_{3-4}$ olefin stream comprising propylene and butene and an isobutane stream comprising isobutane in the $H_2SO_4$ alkylation process section in the presence of an acid catalyst comprising $H_2SO_4$ to produce a reaction mixture comprising alkylate, unreacted propylene, unreacted normal butene, $H_2SO_4$ catalyst, and spent $H_2SO_4$ catalyst; separating the reaction mixture into an alkylate stream, an $H_2SO_4$ catalyst stream, the acid ASO stream comprising spent $H_2SO_4$ catalyst, the acid gas stream, the acid liquid stream, and a stream comprising at least one of the unreacted propylene and the unreacted normal butene; thermally oxidizing at least one of the acid ASO stream, the acid gas stream, and the acid liquid stream.

In some embodiments, the process further comprises: neutralizing at least one of the acid ASO stream, the acid gas stream, the acid liquid stream with caustic forming at least one of the neutralized ASO stream, the neutralized gas stream, the neutralized liquid stream, and a spent caustic stream; thermally oxidizing at least one of the neutralized ASO stream, the neutralized gas stream, the neutralized liquid stream, and the spent caustic stream.

In some embodiments, the process further comprises: introducing at least one of the neutralized ASO stream into a neutralized ASO surge tank before thermally oxidizing the neutralized ASO stream and introducing the neutralized liquid stream into a neutralized liquid surge tank before thermally oxidizing the neutralized liquid stream.In some embodiments, the process further comprises: introducing at least one the acid ASO stream into an acid ASO surge tank before thermally oxidizing the acid ASO stream, and introducing the acid liquid stream into an acid liquid surge tank before thermally oxidizing the acid liquid stream.

In some embodiments, the ionic liquid alkylation process section is present, further comprising: alkylating a $C_{3-4}$ olefin stream comprising propylene and butene and an isobutene stream comprising isobutane in the ionic liquid alkylation process section in the presence of an acid catalyst comprising an ionic liquid to produce a reaction mixture comprising alkylate, unreacted propylene, unreacted normal butene, ionic liquid catalyst, and spent ionic liquid catalyst; separating the reaction mixture into an alkylate stream, an ionic liquid catalyst stream, the acid spent ionic liquid stream comprising spent ionic liquid catalyst, the acid gas stream, the acid liquid stream, and a stream comprising at least one of the unreacted propylene and the unreacted normal butene; thermally oxidizing at least one of the acid spent ionic liquid stream, the acid gas stream, and the acid liquid stream.

In some embodiments, the process further comprises: neutralizing at least one of the acid spent ionic liquid stream, the acid gas stream, and the acid liquid stream with caustic forming at least one of the neutralized spent ionic liquid stream, a neutralized gas stream, a neutralized liquid stream, and a spent caustic stream; thermally oxidizing at least one of the neutralized spent ionic liquid stream, the neutralized gas stream, the neutralized liquid stream, and the spent caustic stream.

In some embodiments, the process further comprises: introducing at least one of the neutralized spent ionic liquid stream into an neutralized ionic liquid surge tank before thermally oxidizing the neutralized spent ionic liquid stream, and introducing the neutralized liquid stream into a neutralized liquid surge tank or both before thermally oxidizing the neutralized liquid stream.

In some embodiments, the process further comprises: introducing at least one of the acid spent ionic liquid stream into an acid spent ionic liquid surge tank before thermally oxidizing the acid spent ionic liquid, and introducing the acid liquid stream to an acid liquid surge tank before thermally oxidizing the acid liquid stream.

In some embodiments, the ionic liquid comprises a chloroaluminate ionic liquid.Another aspect of the invention is a process for treating off-gas and waste effluent streams in an alkylation complex. In one embodiment, the process comprises: alkylating a $C_{3-4}$ olefin stream comprising propylene and butene and an isobutane stream comprising isobutene in an liquid acid alkylation process section or an ionic liquid alkylation process section in the presence of an acid catalyst to produce a reaction mixture comprising alkylate, unreacted propylene, unreacted normal butene, acid catalyst, and spent acid catalyst, wherein the acid catalyst comprises HF, $H_2SO_4$, or an ionic liquid; separating the reaction mixture into at least one of: and alkylate stream, the acid ASO stream, an acid gas stream from the liquid acid alkylation process section, an acid liquid stream from the liquid and an acid alkylation process section; or an acid spent ionic liquid from an ionic liquid alkylation process section, an acid gas stream from the ionic liquid alkylation process section, an acid liquid stream from the ionic liquid alkylation process section, and a stream comprising at least one of the unreacted propylene and the unreacted normal butene; thermally oxidizing at least one of: the acid ASO stream, the acid gas stream from the liquid acid alkylation process section, the acid liquid stream from the liquid acid alkylation process section, a neutralized ASO stream from a caustic wash zone, and a spent caustic stream from an acid gas scrubber zone; or the acid spent ionic liquid from an ionic liquid alkylation process section, the acid gas stream from the ionic liquid alkylation process section, the acid liquid stream from the ionic liquid alkylation process section, a neutralized spent ionic liquid from an ionic liquid caustic wash zone, and a spent caustic stream from an acid gas scrubber zone; in a thermal oxidation system, comprising; thermally oxidizing the at least one of: the acid ASO stream from the liquid acid alkylation process section, the acid gas stream from the liquid acid alkylation process section, the acid liquid stream from the liquid acid alkylation process section, the acid spent ionic liquid from the ionic liquid alkylation process section, the acid gas stream from the ionic liquid alkylation process section, the neutralized ASO stream from the caustic wash zone, and the spent caustic stream from the acid gas scrubber zone; or the acid liquid stream from the ionic liquid alkylation process section, the neutralized spent ionic liquid from the ionic liquid caustic wash zone, and the spent caustic stream from the acid gas scrubber zone, in a thermal oxidizing section forming flue gas consisting essentially of at least one of $H_2O$, $CO_2$, $N_2$, $O_2$, SOx, NOx, HCl, $Cl_2$, HF, $F_2$, $Na_2O$, $Na_2SO_3$, $Na_2SO_4$, $Na_2CO_3$, NaCl, NaF, $CaF_2$, CaO, $CaSO_3$, $CaSO_4$, $CaCO_3$, $CaCl_2$, $K_2O$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO; optionally recovering waste heat from the flue gas in a waste heat recovery section; removing at least one of SOx, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO from the flue gas in a contaminant removal section to form a decontaminated outlet flue gas consisting essentially of at least one of $H_2O$, $CO_2$, $N_2$, $O_2$, and NOx, wherein removing the at least one of SOx, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO from the flue gas comprises: quenching the flue gas in a quench section to form quenched flue gas after recovering the waste heat; and contacting a caustic solution with the quenched flue gas in a contaminant scrubbing section to form the decontaminated outlet flue gas and a liquid stream comprising at least one of $H_2O$, NaCl, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO; or reacting the flue gas with a reactant in a contaminant reaction section to form a reaction section flue gas consisting essentially of at least one of $H_2O$, $CO_2$, $N_2$, $O_2$, $Na_2SO_4$, $Na_2CO_3$, NaCl, NaF, $CaF_2$, $CaSO_4$, $CaCO_3$, $CaCl_2$, $K_2SO_4$, $K_2CO_3$, KCl, KF, $Al_2O_3$, NiO, FeO, $FeO_2$, $Fe_2O_3$, $Fe_3O_4$, and CuO wherein the reactant comprises at least one of $NaHCO_3$, $NaHCO_3 \cdot Na_2CO_3 \cdot 2(H_2O)$, $CaCO_3$ and $Ca(OH)_2$; and filtering the reaction section flue gas in a filtration section to remove $Na_2SO_4$, $Na_2CO_3$, NaCl, NaF, $CaF_2$, $CaSO_4$, $CaCO_3$, $CaCl_2$, $K_2SO_4$, $K_2CO_3$, KCl, KF, $Al_2O_3$, NiO, FeO, $FeO_2$, $Fe_2O_3$, $Fe_3O_4$, and CuO to form the decontaminated outlet flue gas; and optionally removing NOx from the decontaminated outlet flue gas in an NOx removal section to form a de-NOx outlet flue gas consisting essentially of at least one of $H_2O$, $CO_2$, $N_2$, and $O_2$.

In some embodiments, the process further comprises: neutralizing at least one of the acid ASO stream, the acid gas stream from the liquid acid alkylation process section, the acid liquid stream from the liquid acid alkylation process section, the acid spent ionic liquid stream, the acid gas stream from the ionic liquid alkylation process section, the acid liquid stream from the ionic liquid alkylation process section with caustic forming the neutralized ASO stream, a neutralized gas stream from the liquid acid alkylation process section, a neutralized liquid stream from the liquid acid alkylation process section, the neutralized spent ionic liquid stream, a neutralized gas stream from the ionic liquid alkylation process section, a neutralized liquid stream from the ionic liquid alkylation process section, and the spent caustic stream; thermally oxidizing at least one of the neutralized ASO stream, the neutralized liquid stream from the liquid acid alkylation process section the neutralized spent ionic liquid stream, the neutralized liquid stream from the ionic gas alkylation process section, the neutralized liquid stream from the ionic liquid alkylation process section, and the spent caustic stream.

In some embodiments, the process further comprises: introducing at least one of: the neutralized ASO stream into a neutralized ASO surge tank before thermally oxidizing the neutralized ASO stream, the neutralized liquid stream from the liquid acid alkylation process section into a neutralized liquid surge tank before thermally oxidizing the neutralized liquid stream, the neutralized spent ionic liquid stream into a neutralized spent ionic liquid surge tank before thermally oxidizing the neutralized spent ionic liquid stream, the neutralized liquid stream from the ionic gas alkylation process section into a neutralized liquid surge tank before thermally oxidizing the neutralized liquid stream, and the spent caustic stream into a spent caustic surge tank before thermally oxidizing the spent caustic stream.

In some embodiments, the ionic liquid comprises a chloroaluminate ionic liquid.

The paraffin used in the alkylation process preferably comprises an isoparaffin having from 4 to 10 carbon atoms, or 4 to 8 carbon atoms, or 4 to 5 carbon atoms. The olefin used in the alkylation process preferably has from 2 to 10 carbon atoms, or 3 to 8 carbon atoms, or 3 to 5 carbon atoms.

One application of the alkylation process is to upgrade low value $C_3$ and $C_4$ hydrocarbons to higher value alkylates. To that extent, one specific embodiment is the alkylation of butanes with propylene and butene to generate $C_{7-8}$ compounds. Preferred products include trimethylpentane (TMP), and while other $C_8$ isomers are produced, one competing isomer is dimethylhexane (DMH). The quality of the product stream can be measured in the ratio of TMP to DMH, with a high ratio desired.

The isoparaffin and olefin are sent to an alkylation process section. The alkylation process section can be a liquid acid alkylation process section or an ionic liquid alkylation process section. The alkylation process section includes a liquid acid alkylation catalyst or an ionic liquid catalyst to react the olefin with the isoparaffin to generate alkylate. The liquid acid alkylation process section can use a liquid acid, such as HF or $H_2SO_4$. The ionic liquid alkylation process section can use any suitable acid ionic liquid. Suitable acid ionic liquid catalysts are described in US Pat. No. 10,369,556, for example. Suitable acid ionic liquids, include, but are not limited to, chloroaluminate ionic liquids.

HF alkylation processes, $H_2SO_4$ alkylation processes, and ionic liquid alkylation processes are known in the art (e.g., HF alkylation: U.S. Pat. Nos. 4,774375, 4,891,466, 5,763,728, 5,948,947, and EP 0 320 094; $H_2SO_4$ alkylation: U.S. Pat. Nos. 7,652,187, and 7,977,525; ionic liquid alkylation U.S. Pat. Nos. 8,329,603, 9,079, 816, 9,181,150, 9,302,951, 9,328,037, 9,399,604, 9,914,675, and 10,369,556; each of which is incorporated herein by reference).

Alkylation reaction temperatures are typically in the range of from about 5° C. to about 150° C. Lower temperatures favor alkylation reaction of isoparaffins with olefins over competing olefin side reactions such as oligomerization and polymerization. However, overall reaction rates decrease with decreasing temperatures. Temperatures within the given range, and preferably in the range of from about 30° C. to about 130° C., provide good selectivity for alkylation of isoparaffins with olefins at commercially attractive reaction rates.

Reaction pressures in the alkylation reaction zone may range from pressures sufficient to maintain reactants in the liquid phase to about 1.5 MPa (g). Reactant hydrocarbons may be normally gaseous at alkylation reaction temperatures. Reaction pressures in the range of from about 276 kPa (g) (40 psig) to about 1.1 MPa (g) (160 psig) are suitable. With all reactants in the liquid phase, increased pressure has no significant effect upon the alkylation reaction.

When ionic liquid catalysts are used, the temperature is typically in the range of about –20° C. to the decomposition temperature of the ionic liquid, or about –20° C. to about 100° C., for example. The pressure is typically in the range of atmospheric (0.1 MPa (g)) to about 8.0 MPa (g), or about 0.3 MPa (g) to about 2.5 MPa (g).

Contact times for hydrocarbon reactants in an alkylation reaction zone, in the presence of the alkylation catalyst composition of the present invention generally should be sufficient to provide for essentially complete conversion of olefin reactants in the alkylation zone. Preferably, the contact time is in the range of from about 0.05 minute to about 60 minutes.

Appropriate reaction conditions for the specific alkylation process can be selected by those skilled in art.

The liquid acid alkylation process and ionic liquid alkylation process produce a reaction mixture comprising alkylate, unreacted propylene, unreacted butene, normal butane, acid catalyst, and spent acid catalyst. When the liquid acid alkylation process is used, the spent acid catalyst is acid ASO, and when the ionic liquid process is used, the spent acid catalyst is acid spent ionic liquid. The reaction mixture is separated into alkylate stream, a propylene stream, a normal butene stream, an acid catalyst stream, and the acid ASO stream or the acid spent ionic liquid stream, In either case, an acid gas stream, and an acid liquid stream are formed.

At least one of the acid ASO stream or the acid spent ionic liquid stream, the acid gas stream, and the acid liquid stream can be thermally oxidized in a thermal oxidation system.

Alternatively, the acid ASO stream or the acid spent ionic liquid stream can be neutralized with caustic forming a neutralized ASO stream or a neutralized spent ionic liquid stream. In this case, at least one of the neutralized ASO stream or the neutralized spent ionic liquid stream can be thermally oxidized in the thermal oxidation system.

The thermal oxidation system may comprise a thermal oxidizing section, an optional waste heat recovery section, a contaminant removal section comprising a quench section and a contaminant scrubbing section, and an optional NOx removal section.

Alternatively, the thermal oxidation system may comprise a thermal oxidizing section, an optional waste heat recovery section, a contaminant removal section comprising a contaminant reaction section and a filtration section, and an optional NOx removal section.

The flue gas produced in the thermal oxidation section and the compounds removed depend on the type of alkylation process used and the type of contaminant removal used.

When the HF alkylation process is used, the flue gas from the thermal oxidation section consisting essentially of at least one of $H_2O$, $CO_2$, $N_2$, $O_2$, SOx, NOx, HCl, $Cl_2$, HF, $F_2$, $Na_2O$, $Na_2SO_3$, $Na_2SO_4$, $Na_2CO_3$, NaCl, NaF, $CaF_2$, CaO, $CaSO_3$, $CaSO_4$, $CaCO_3$, $CaCl_2$, $K_2O$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO.

In this case, when the contaminant removal section comprises the contaminant scrubbing section, at least one of NaCl, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO are removed in a liquid stream from the flue gas following contact with caustic.

When the contaminant removal section comprises the contaminant reaction section, the flue gas is reacted with at least one of $NaHCO_3$, $NaHCO_3.Na_2CO_3.2(H_2O)$, $CaCO_3$ and $Ca(OH)_2$. The flue gas is then filtered in a filtration section to remove at least one of $Na_2SO_4$, $Na_2CO_3$, NaCl, NaF, $CaF_2$, $CaSO_4$, $CaCO_3$, $CaCl_2$, $K_2SO_4$, $K_2CO_3$, KCl, KF, $Al_2O_3$, NiO, FeO, $FeO_2$, $Fe_2O_3$, $Fe_3O_4$, and CuO.

When the $H_2SO_4$ alkylation process is used, the flue gas from the thermal oxidation section consisting essentially of at least one of $H_2O$, $CO_2$, $N_2$, $O_2$, SOx, NOx, HCl, $Cl_2$, $Na_2O$, $Na_2SO_3$, $Na_2SO_4$, $Na_2CO_3$, NaCl, CaO, $CaSO_3$, $CaSO_4$, $CaCO_3$, $CaCl_2$, $K_2O$, $K_2SO_3$, $K_2SO_4$, $K_2CO_3$, KCl, $Al_2O_3$, NiO, FeO, $FeO_2$, $Fe_2O_3$, $Fe_3O_4$, and CuO.

In this case, when the contaminant removal section comprises the contaminant scrubbing section, at least one of NaCl, HCl, $Cl_2$, $Na_2SO_3$, $Na_2SO_4$, $Na_2CO_3$, NaCl, $CaSO_3$, $CaSO_4$, $CaCO_3$, $CaCl_2$, $K_2SO_3$, $K_2SO_4$, $K_2CO_3$, KCl, $Al_2O_3$, NiO, FeO, $FeO_2$, $Fe_2O_3$, $Fe_3O_4$, and CuO are removed in a liquid stream from the flue gas following contact with caustic.

When the contaminant removal section comprises the contaminant reaction section, the flue gas is reacted with at least one of $NaHCO_3$, $NaHCO_3.Na_2CO_3.2(H_2O)$, $CaCO_3$ and $Ca(OH)_2$. The flue gas is then filtered in a filtration section to remove at least one of $Na_2SO_4$, $Na_2CO_3$, NaCl, $CaSO_4$, $CaCO_3$, $CaCl_2$, $K_2SO_4$, $K_2CO_3$, KCl, $Al_2O_3$, NiO, FeO, $FeO_2$, $Fe_2O_3$, $Fe_3O_4$, and CuO.

In the case of ionic liquid alkylation, the flue gas from the thermal oxidation section consisting essentially of at least one of $H_2O$, $CO_2$, $N_2$, $O_2$, SOx, NOx, HCl, $Cl_2$, HF, $F_2$, $Na_2O$, $Na_2SO_3$, $Na_2SO_4$, $Na_2CO_3$, NaCl, NaF, $CaF_2$, CaO, $CaSO_3$, $CaSO_4$, $CaCO_3$, $CaCl_2$, $K_2O$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO.

In this case, when the contaminant removal section comprises the contaminant scrubbing section, at least one of $H_2O$, NaCl, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO are removed in a liquid stream from the flue gas following contact with caustic.

When the contaminant removal section comprises the contaminant reaction section, the flue gas is reacted with at least one of $NaHCO_3$, $NaHCO_3.Na_2CO_3.2(H_2O)$, $CaCO_3$ and $Ca(OH)_2$. The flue gas is then filtered in a filtration section to remove at least one of $Na_2SO_4$, $Na_2CO_3$, NaCl, NaF, $CaF_2$, $CaSO_4$, $CaCO_3$, $CaCl_2$, $K_2SO_4$, $K_2CO_3$, KCl, KF, $Al_2O_3$, NiO, FeO, $FeO_2$, $Fe_2O_3$, $Fe_3O_4$, and CuO.

If the flue gas comprises NOx, there will be a NOx removal section.

FIG. 1 illustrates one embodiment of a prior art alkylation process 100. A $C_{3-4}$ stream 105 comprising propylene and butene and an isobutane stream 110 comprising isobutane are sent to a liquid acid alkylation process section 115. The $C_{3-4}$ stream 105 can be a treated stream from a fluid catalytic cracking (FCC) reactor or a treated stream from a coker reactor.

The liquid acid alkylation process section 115 contains a liquid acid catalyst. The liquid acid alkylation process section 115 can be an HF alkylation process section using HF as the liquid acid catalyst, an $H_2SO_4$ alkylation process section as the liquid acid catalyst, or an ionic liquid alkylation process section as the liquid acid catalyst. HF alkylation, $H_2SO_4$ alkylation, and an ionic liquid alkylation processes are well-known in the art.

The liquid acid alkylation reaction of the $C_{3-4}$ stream 105 and isobutane stream 110 produces alkylate. Alkylate stream 120 comprising alkylate, an unreacted propylene stream 125, and an unreacted normal butene stream 130 exit the liquid acid alkylation process section 115. The unreacted propylene stream 125 and the unreacted normal butene stream 130 can be recycled to the liquid acid alkylation process section115. The alkylate stream 120 can be recovered.

The alkylation reaction forms acid ASO for HF and $H_2SO_4$ alkylation or acid spent ionic liquid for ionic liquid alkylation as a byproduct of the alkylation reaction. When too much ASO or acid spent ionic liquid is present, the liquid acid catalyst loses its effectiveness. The acid ASO stream 135 or acid spent ionic liquid stream 140 is removed from the liquid acid alkylation process section 115 for treatment.

The acid ASO stream 135 or acid spent ionic liquid stream 140 is sent to a caustic wash zone 145. Caustic stream 150, such as NaOH, or KOH, is contacted with the acid ASO stream 135 or acid spent ionic liquid stream 140 to neutralize the acid. The neutralized ASO stream 155 can be used, i.e., as fuel oil, fuel for the isostripper fired heater reboiler, or feed to a fluid catalytic cracking (FCC) reactor. Neutralized spent ionic liquid stream 160 can be sent to a coker reactor, or to a landfill or other offsite waste disposal facility.

There can be an acid gas stream 170 exiting the liquid acid alkylation process section 115. The acid gas stream 170 can comprise gas streams including, but not limited to, a vent gas absorber, relief valves, service pumps vents, polymer neutralizer, constant boiling mixture (CBM) neutralizer, KOH regenerator, isostripper overhead knockout drum, relief gas scrubber, or combinations thereof. The acid gas stream 170 is sent to an acid gas scrubbing zone 175. A caustic stream 180 is introduced into the acid gas scrubbing zone 175 to neutralize the acid gas stream 170. The sweet gas stream 185 can be burned. The spent caustic stream 187 can be treated by treated by neutralization, wet air oxidation, or thermal oxidation.

There can also be an acid liquid stream 190 from an acid gas knockout drum, or an acid sewer system exiting the liquid acid alkylation process section 115. The acid liquid stream 190 may contain HF, $H_2SO_4$, or ionic liquid. The acid liquid stream 190 can be sent to a neutralization basin 195, where it is neutralized with a caustic stream 197. The neutralized liquid stream 200 can be sent to a waste water treatment facility.

Figure 2:
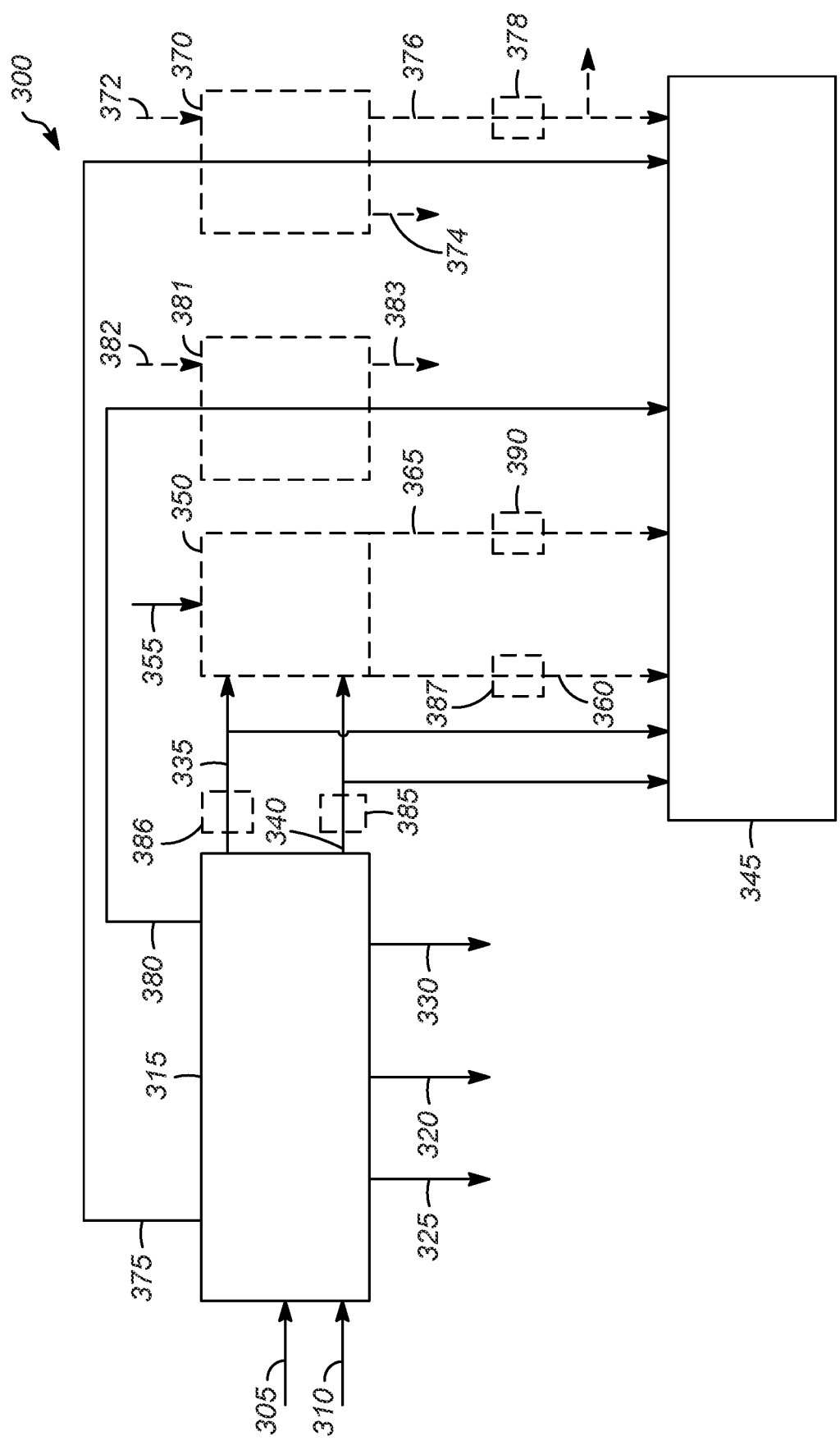
FIG. 2 is an illustration of one embodiment of an alkylation process according to the present invention.

FIG. 2 illustrates one embodiment of an alkylation process 300 according to the present invention. A $C_{3-4}$ stream 305 comprising propylene and butene and an isobutane stream 310 comprising isobutane are sent to a liquid acid alkylation process section 315. The liquid acid alkylation process section 315 contains a liquid acid catalyst.

The liquid acid alkylation process section 315 can be an HF alkylation process section, an $H_2SO_4$ alkylation process section, or an ionic liquid alkylation process section, as discussed above.

The liquid acid alkylation reaction of the $C_{3-4}$ stream 305 and isobutane stream 310 produces alkylate. Alkylate stream 320 comprising alkylate, an unreacted propylene stream 325, and an unreacted normal butene stream 330 exit the liquid acid alkylation process section 315. The unreacted propylene stream 325 and the unreacted normal butene stream 330 can be recycled to the liquid acid alkylation process section 315. The alkylate stream 120 can be recovered.

The acid ASO stream 335 or acid spent ionic liquid stream 340 may be sent directly to the thermal oxidation system 345.

Alternatively, acid ASO stream 335 or acid spent ionic liquid stream 340 may be sent to a caustic wash zone 350. Caustic stream 355, is contacted with the acid ASO stream 335 or acid spent ionic liquid stream 340 to neutralize the acid. The neutralized ASO stream 360 or neutralized spent ionic liquid stream 365 can be sent to thermal oxidation system 345.

The acid gas stream 375 can be sent directly to the thermal oxidation system 345. Alternatively, the acid gas stream 375 could be sent to an acid gas scrubbing zone 370. This might be needed with HF alkylation because the high vapor pressure of HF (Reid vapor pressure 783 mm Hg at 20° C.) would lead to an unacceptably high HF content in the acid gas stream 375 in emergency situations. This would not be the case with ionic liquid alkylation and $H_2SO_4$ due to the low vapor pressure of ionic liquids (Reid vapor pressure less than 5.2 mm Hg at 20° C.) and $H_2SO_4$ (Reid vapor pressure 0.001 mm Hg at 20° C.) relative to HF. A caustic stream 372 is introduced into the acid gas scrubbing zone 370 to neutralize the acid gas stream 375. The sweet gas stream 374 can be burned. The spent caustic stream 376 can be treated by treated by neutralization, wet air oxidation, or thermal oxidation.

The acid liquid stream 380 can be sent directly to the thermal oxidation system 345. Alternatively, the acid liquid stream 380 could be sent to a neutralization basin 381, where it is neutralized with a caustic stream 382. The neutralized liquid stream 383 can be sent to a waste water treatment facility. In some embodiments, there could be an acid spent ionic liquid surge tank 385 between the liquid acid alkylation process section 315 and the thermal oxidation system 345 to provide a controlled amount of acid spent ionic liquid to the thermal oxidation system 345. Alternatively or in addition, there could be an acid ASO surge tank 386 between the liquid acid alkylation process section 315 and the thermal oxidation system 345. Alternatively or in addition, there could be a neutralized spent ionic liquid surge tank 390 between the caustic wash zone 350 and the thermal oxidation system 345 to provide a controlled amount of neutralized spent ionic liquid to the thermal oxidation system 345. Alternatively or in addition, there could be a neutralized ASO surge tank 387 between the caustic wash zone 350 and the thermal oxidation system 345 to provide a controlled amount of neutralized ASO to the thermal oxidation system 345. Alternatively or in addition, there could be a spent caustic surge tank 378 between the acid gas scrubbing zone 370 and the thermal oxidation system 345 to provide a controlled amount of spent caustic to the thermal oxidation system 345.

Figure 3:
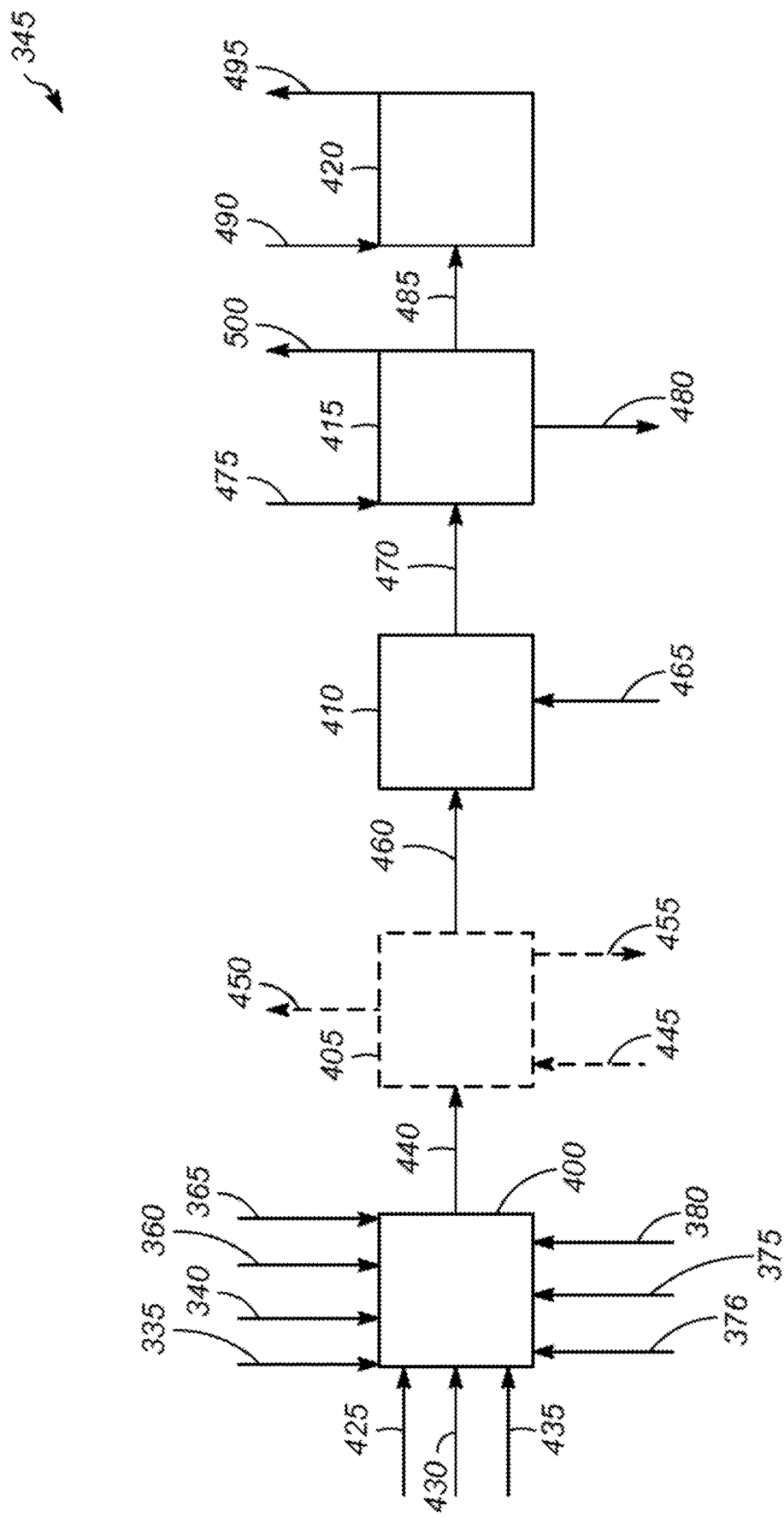
FIG. 3 is an illustration of one embodiment of a thermal oxidation system according to the present invention.

One embodiment of a thermal oxidation system 345 is illustrated in FIG. 3. The thermal oxidation system 345 comprises a thermal oxidizing section 400, an optional waste heat recovery section 405, a quench section 410, a contaminant scrubbing section 415, and an optional NOx removal section 420.

At least one of the acid ASO stream 335, the acid spent ionic liquid stream 340, the neutralized ASO stream 360, the neutralized spent ionic liquid stream 365, the spent caustic stream 376, the acid gas stream 375, and the acid liquid stream 380, along with a combustion air stream 425, make-up natural gas or fuel gas stream 430 (as needed), and quench stream 435 (as needed) are introduced into the thermal oxidizing section 400. The inlet temperature of the thermal oxidizing section 400 is typically in the range of −30-500° C. with a pressure of −1 kPa(g) to 3000 kPa(g). The outlet temperature is typically in the range of 650-1300° C. with a pressure of −1 kPa(g) to 50 kPa(g). The residence time in the thermal oxidizing section 400 is between 0.5 and 2 seconds. The thermal oxidizing section 400 can be forced draft, induced draft, or a combination of both. An optional selective non-catalytic reduction (SNCR) section may be present in some cases. The inlet temperature of the SNCR section is typically in the range of 650-1300° C with a pressure of −1 kPa(g) to 50 kPa(g). The outlet temperature is typically in the range of 650-1040° C. with a pressure of −1 kPa(g) to 50 kPa(g). The residence time in the SNCR section is between 0.2 and 1 seconds. The thermal oxidation step would be separated from the SNCR step via a choke wall in the vessel. The hydrocarbons are converted to $H_2O$ and $CO_2$. The sulfides from the sulfur species (e.g., $H_2S$) present in feed are converted to oxidized sulfur particulate SOx including, but not limited to, $SO_2$ and $SO_3$, and $H_2O$. The nitrogen from the nitrogen bound molecules (e.g. $NH_3$) present in the feed are converted to Nitrogen ($N_2$) and NOx, including but not limited to NO, $NO_2$. The HCl and $Cl_2$ (if any) remain. Any metals in the streams will be oxidized, including, but not limited to, NiO, FeO, $FeO_2$, $Fe_2O_3$, $Fe_3O_4$, and CuO. The metal component in the ionic liquid will be oxidized. For example, butyl pyridinium heptachloroaluminate will be oxidized to a mixture of $CO_2$, $H_2O$, $N_2$, NOx, HCl, $Cl_2$, and $Al_2O_3$.

The flue gas stream 440 from the thermal oxidizing section 400 consists essentially of at least one of $H_2O$, $CO_2$, $N_2$, $O_2$, SOx, NOx, HCl, $Cl_2$, HF, $F_2$, $Na_2O$, $Na_2SO_3$, $Na_2SO_4$, $Na_2CO_3$, NaCl, NaF, $CaF_2$, CaO, $CaSO_3$, $CaSO_4$, $CaCO_3$, $CaCl_2$, $K_2O$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO. "Consisting essentially of" means that one of more of the gases or vapors are present and there are no other gases or vapors present which require treatment before being released to the atmosphere, The flue gas stream 440 is sent to the optional waste heat recovery section 405. The inlet temperature of the optional waste heat recovery section 405 is typically in the range of 650-1300° C. with a pressure of −2 kPa(g) to 50 kPa(g). The outlet temperature is typically in the range of 200-400° C. with a pressure of −2 kPa(g) to 50 kPa(g). Suitable waste heat recovery apparatus and methods include, but are not limited to, a waste heat recovery boiler, including, but not limited to, a firetube boiler or a watertube boiler. Boiler feed water or oil stream 445 enters the waste heat recovery section 405 where a portion is converted to steam or hot oil stream 450, with the remainder exiting as blow-down water or oil stream 455. In some cases, the steam can be converted to electricity, for example using a steam turbine, if desired.

The recovered waste heat in steam or hot oil stream 450 can be in the form of low (e.g., less than 350 kPa(g)), medium (e.g., 350 kPa(g) to 1750 kPa(g)), or high (e.g., greater than 1750 kPa(g)) pressure saturated or superheated steam, hot oil, and/or electricity. The recovered heat can be used to provide heat to at least one pieces of equipment or process streams in the alkylation complex or to other parts of the plant. For example, the recovered waste heat in steam or hot oil stream 450 can be used in reboilers for a variety of columns, such as an isostripper column, a depropanizer column, an HCL stripper column, a rerun column, and an HF stripper column or other areas of the plant, or for other heat requirements.

The flue gas stream 460 from the optional waste heat recovery section 405 flows to the quench section 410 where the temperature of the flue gas is reduced to the saturation temperature using quench stream 465. The inlet temperature of the quench section 410 is typically in the range of 200-400° C. with a pressure of −3 kPa(g) to 50 kPa(g). The inlet temperature could be up to 1300° C. if no waste heat reboiler is present. The outlet temperature is typically in the range of 45-150° C. with a pressure of −3 kPa(g) to 50 kPa(g). Quench stream 465 includes, but is not limited to, water, air, recycle flue gas, or combinations thereof.

The quenched flue gas stream 470 from the quench section 410 is sent to the contaminant scrubbing section 415 for removal of at least one of the SOx, HCl, $Cl_2$, HF, $F_2$, $Na_2O$, $Na_2SO_3$, $Na_2SO_4$, $Na_2CO_3$, NaCl, NaF, $CaF_2$, CaO, $CaSO_3$, $CaSO_4$, $CaCO_3$, $CaCl_2$, $K_2O$, $K_2SO_3$, $K_2SO_4$, $K_2CO_3$, KCl, KF, $Al_2O_3$, NiO, FeO, $FeO_2$, $Fe_2O_3$, $Fe_3O_4$, $Al_2O_3$, and CuO. The inlet temperature of the contaminant scrubbing section 415 is typically in the range of 45-150° C. with a pressure of −4 kPa(g) to 50 kPa(g). The outlet temperature is typically in the range of 45-150° C. with a pressure of −4 kPa(g) to 50 kPa(g). For example, in the contaminant scrubbing section 415, a caustic stream 475 comprising aqueous NaOH is introduced into the scrubbing section where it reacts with the at least one of compounds in the flue gas. An aqueous stream 480 containing at least one of $H_2O$, NaCl, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO exits the scrubbing section. If desired, a reducing agent such as $NaHSO_3$ or $H_2O_2$, can be included to react with the $Cl_2$ to form HCl which reacts to form NaCl.

The contaminant outlet flue gas stream 485 from the contaminant scrubbing section 415 has a reduced level of at least one of $H_2O$, NaCl, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO compared to the incoming quenched flue gas stream 470. The contaminant outlet flue gas stream 485 comprises at least one of $H_2O$, $CO_2$, $N_2$, $O_2$, and NOx.

If NOx is present in the contaminant outlet flue gas stream 485, the contaminant outlet flue gas stream 485 is sent to the optional NOx removal section 420 to remove NOx. The inlet temperature of the NOx removal section 420 is typically in the range of 150-300° C. with a pressure of −5 kPa(g) to 50 kPa(g). The outlet temperature is typically in the range of 200-350° C. with a pressure of −5 kPa(g) to 50 kPa(g). The contaminant outlet flue gas stream 485 may need to be heated to obtain the desired inlet temperature for the NOx removal section 420. For example, the NOx removal section 420 can be a selective catalytic reduction (SCR) section in which an ammonia and/or urea stream 490 are introduced into the SCR section where it reacts with the NOx and forms N2 and H2O. Any suitable SCR catalyst could be used, including but not limited to, ceramic carrier materials such as titanium oxide with active catalytic components such as oxides of base metals including $TiO_2$, $WO_3$ and $V_2O_5$, or an activated carbon based catalyst. The de-NOx outlet flue gas stream 495 comprises at least one of $H_2O$, $CO_2$, $N_2$, and $O_2$.

If the contaminant outlet flue gas stream 485 does not contain NOx, the optional NOx removal section 420 is not present. The contaminant outlet flue gas stream 500, consisting essentially of at least one of $H_2O$, $CO_2$, $N_2$, and $O_2$, can be vented to the atmosphere.

Figure 4:
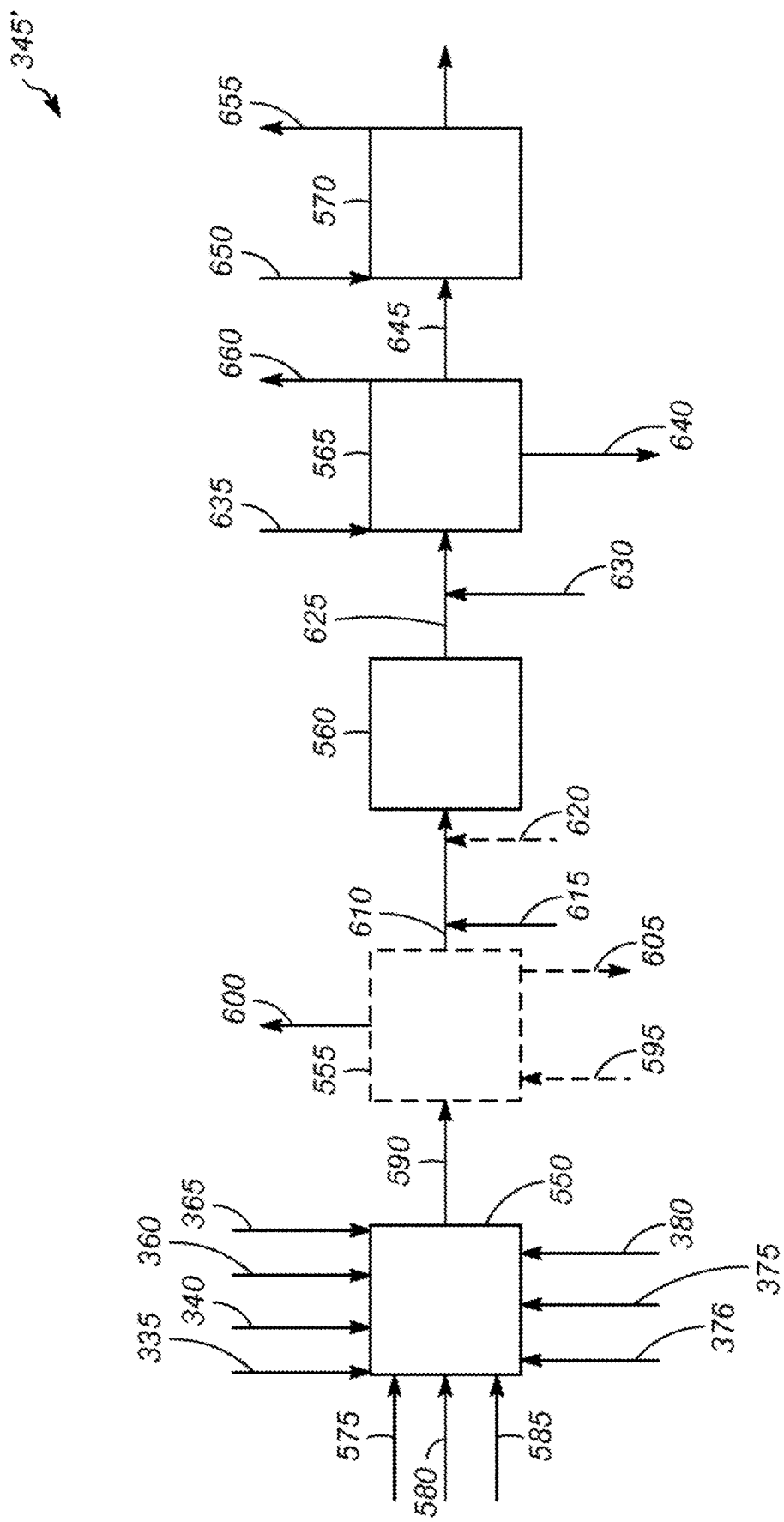
FIG. 4 is an illustration of another embodiment of a thermal oxidation system according to the present invention.

Another embodiment of the thermal oxidation system 345' is illustrated in FIG. 4. The thermal oxidation system 345' comprises a thermal oxidizing section 550, an optional waste heat recovery section 555, a contaminant removal section 560, a filtration section 565, and an optional NOx removal section 570.

At least one of the acid ASO stream 335, the acid spent ionic liquid stream 340, the neutralized ASO stream 360, the neutralized spent ionic liquid stream 365, the spent caustic stream 376, the acid gas stream 375, and the acid liquid stream 380, along with a combustion air stream 575, make-up natural gas or fuel gas stream 580 (as needed), and quench stream 585 (as needed) are introduced into the thermal oxidizing section 550, as described above.

The inlet temperature of the thermal oxidizing section 550 is typically in the range of –30-500° C. with a pressure of –1 kPa(g) to 3000 kPa(g). The outlet temperature is typically in the range of 650-1300° C. with a pressure of –1 kPa(g) to 50 kPa(g). The residence time in the thermal oxidizing section 550 is between 0.5 and 2 seconds. Any suitable thermal oxidizing section 550 could be used. The thermal oxidizing section 550 can be forced draft, induced draft, or a combination of both. The inlet temperature of the optional SNCR section is typically in the range of 650-1300° C with a pressure of –1 kPa(g) to 50 kPa(g). The outlet temperature is typically in the range of 650-1040° C. with a pressure of –1 kPa(g) to 50 kPa(g). The residence time in the SNCR section is between 0.2 and 1 seconds. The thermal oxidation step would be separated from the SNCR step via a choke wall in the vessel.

The flue gas stream 590 from the thermal oxidizing section 550 comprises at least one of $H_2O$, $CO_2$, $N_2$, $O_2$, SOx, NOx, HCl, $Cl_2$, HF, $F_2$, $Na_2O$, $Na_2SO_3$, $Na_2SO_4$, $Na_2CO_3$, NaCl, NaF, $CaF_2$, CaO, $CaSO_3$, $CaSO_4$, $CaCO_3$, $CaCl_2$, $K_2O$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO. The flue gas stream 590 is sent to the optional waste heat recovery section 555. Boiler feed water or oil stream 595 enters the optional waste heat recovery section 555 where a portion is converted to steam or hot oil stream 600, with the remainder exiting as blowdown water or oil 605. The inlet temperature of the optional waste heat recovery section 555 is typically in the range of 650-1300° C. with a pressure of –2 kPa(g) to 50 kPa(g). The outlet temperature is typically in the range of 200-400° C. with a pressure of –2 kPa(g) to 50 kPa(g). Suitable waste heat recovery apparatus and methods are described above. The recovered waste heat in steam or hot oil stream 600 can be in the form of low, medium, or high pressure saturated or superheated steam, hot oil, and/or electricity. The recovered waste heat in steam or hot oil stream 600 can be used in reboilers for a variety of columns such as an isostripper, column, a depropanizer column, an HCL stripper column, a rerun column, and an HF stripper column, or elsewhere in the plant, or for other heat requirements.

The flue gas stream 610 from the optional waste heat recovery section 555 is sent to the contaminant removal section 560 to convert at least one of compounds in the flue gas stream 610. The inlet temperature of the contaminant removal section 560 is typically in the range of 200-400° C. with a pressure of –3 kPa(g) to 50 kPa(g). The outlet temperature is typically in the range of 200-400° C. with a pressure of –3 kPa(g) to 50 kPa(g). Fresh sorbent 615 and optionally recycled sorbent 620 (comprising a mixture of at least one of $Na_2CO_3$, $Na_2SO_4$, NaCl, NaF, $K_2CO_3$, $K_2SO_4$, KCl, KF, $CaCO_3$, $CaSO_4$, $CaF_2$, $CaCl_2$, NiO, FeO, $FeO_2$, $FeO_2$, $Fe_2O_3$, $Fe_3O_4$, CuO, depending on the compounds used in the reactant used, as discussed below) can be added to the flue gas stream 610. For example, the contaminant removal section 560 may contain a reactant, such as at least one of $NaHCO_3$, $NaHCO_3.Na_2CO_3.2(H_2O)$, $CaCO_3$ and $Ca(OH)_2$. The reactant reacts with at least one of the SOx, HCl, $Cl_2$, HF, $F_2$, $Na_2SO_3$, $Na_2SO_4$, $Na_2CO_3$, NaCl, NaF, $CaF_2$, $SO_3$, $CaSO_4$, $CaCO_3$,$CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO in the incoming flue gas stream 610. The reaction section flue gas stream 625 has a less of at least one of compounds compared to the incoming flue gas stream 610. The reaction section flue gas stream 625 consists essentially of at least one $H_2O$, $CO_2$, $N_2$, $O_2$, $Na_2SO_4$, $Na_2CO_3$, NaCl, NaF, $CaF_2$, $CaSO_4$, $CaCO_3$, $CaCl_2$, $K_2SO_4$, $K_2CO_3$, KCl, KF, $Al_2O_3$, NiO, FeO, $FeO_2$, $Fe_2O_3$, $Fe_3O_4$, and CuO.

The reaction section flue gas stream 625 is combined with a quench stream 630 comprising air, and/or water, and/or quenched flue gas. The temperature of the reaction section flue gas stream 625 is typically reduced from 200-400° C. with a pressure of –4 kPa(g) to 50 kPa(g) to 150-250° C. with a pressure of –4 kPa(g) to 50 kPa(g). The quenched reaction section flue gas stream 625 is sent to the filtration section 565 for removal of at least one of $Na_2SO_4$, $Na_2CO_3$, NaCl, NaF, $CaF_2$, $CaSO_4$, $CaCO_3$, $CaCl_2$, $K_2SO_4$, $K_2CO_3$, KCl, KF, $Al_2O_3$, NiO, FeO, $FeO_2$, $Fe_2O_3$, $Fe_3O_4$, and CuO. The inlet temperature of the filtration section 565 is typically in the range of 150-350° C. with a pressure of –5 kPa(g) to 50 kPa(g). The outlet temperature is typically in the range of 150-350° C. with a pressure of –5 kPa(g) to 50 kPa(g). The filtration section 565 comprises a bag filter, and/or a ceramic filter, and/or an electrostatic precipitator. An instrument air purge or high voltage DC 635 is introduced into the filtration section 565. In the case of the instrument air purge, it purges the retained material from the filter. In the case of the high voltage stream, it charges the cathodes of the ESP. The particulate is removed from the ESP by vibration. Dry residue stream 640 comprising at least one of $Na_2SO_4$, $Na_2CO_3$, NaCl, NaF, $CaF_2$, $CaSO_4$, $CaCO_3$, $CaCl_2$, $K_2SO_4$, $K_2CO_3$, KCl, KF, $Al_2O_3$, NiO, FeO, $FeO_2$, $Fe_2O_3$, $Fe_3O_4$, and CuO exits the filtration section 565. The filtered flue gas stream 645 comprises at least one of $H_2O$, $CO_2$, $N_2$, $O_2$, and NOx.

If NOx is present in the filtered flue gas stream 645, the filtered flue gas stream 645 is sent to the optional NOx removal section 570 to remove NOx as discussed above.

The inlet temperature of the NOx removal section 570 is typically in the range of 150-300° C. with a pressure of –6 kPa(g) to 50 kPa(g). The outlet temperature is typically in the range of 200-350° C. with a pressure of –6 kPa(g) to 50 kPa(g). For example, the NOx removal section 570 can be a selective catalytic reduction (SCR) section in which an ammonia and/or urea stream 650 are introduced into the SCR section where it reacts with the NOx and forms $N_2$ and $H_2O$. Any suitable SCR catalyst could be used, including but not limited to, ceramic carrier materials such as titanium oxide with active catalytic components such as oxides of base metals including $TiO_2$, $WO_3$ and $V_2O_5$, or an activated carbon based catalyst. The de-NOx outlet flue gas stream 655 consists essentially of at least one of $H_2O$, $CO_2$, $N_2$, and $O_2$.

If the filtered flue gas stream 645 does not contain NOx, the optional NOx removal section 570 is not present. The filtered flue gas stream 660, consisting essentially of at least one of $H_2O$, $CO_2$, $N_2$, and $O_2$, can be vented to the atmosphere.

Any of the above lines, conduits, units, devices, vessels, surrounding environments, zones or similar may be equipped with at least one monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through at least one networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to at least one computing devices or systems. Computing devices or systems may include at least one processor and memory storing computer-readable instructions that, when executed by the at least one processor, cause the at least one computing devices to perform a process that may include at least one steps. For example, the at least one computing devices may be configured to receive, from at least one monitoring component, data related to at least one piece of equipment associated with the process. The at least one computing devices or systems may be configured to analyze the data. Based on analyzing the data, the at least one computing devices or systems may be configured to determine at least one recommended adjustments to at least one parameters of at least one processes described herein. The at least one computing devices or systems may be configured to transmit encrypted or unencrypted data that includes the at least one recommended adjustments to the at least one parameters of the at least one processes described herein.

It should be appreciated and understood by those of ordinary skill in the art that various other components such as valves, pumps, filters, coolers, etc., were not shown in the drawings as it is believed that the specifics of same are well within the knowledge of those of ordinary skill in the art and a description of same is not necessary for practicing or understanding the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

By the term "about," we mean within 10% of the value, or within 5%, or within 1%.

As used herein, the terms "unit," "zone," and "section" can refer to an area including one or more equipment items as appropriate for the type of unit, zone, or section and/or one or more sub-zones or sub-sections. Equipment items can include, but are not limited to, one or more reactors or reactor vessels, separation vessels, adsorbent chamber or chambers, distillation towers, heaters, exchangers, pipes, pumps, compressors, and controllers. Additionally, an equipment item, such as a reactor, dryer, adsorbent chamber or vessel, can further include one or more sections, sub-sections, zones, or sub-zones.

Specific Embodiments

While the following is described in conjunction with specific embodiments, it will be understood that this description is intended to illustrate and not limit the scope of the preceding description and the appended claims.

A first embodiment of the invention is a process for treating off-gas and waste effluent streams in an alkylation complex comprising thermally oxidizing at least one of an acid soluble oil (acid ASO) stream from a liquid acid alkylation process section, an acid gas stream from the liquid acid alkylation process section, an acid liquid stream from the liquid acid alkylation process section, a neutralized ASO stream from a caustic wash zone, and a spent caustic stream from an acid gas scrubber zone; or an acid spent ionic liquid from an ionic liquid alkylation process section, an acid gas stream from the ionic liquid alkylation process section, an acid liquid stream from the ionic liquid alkylation process section, a neutralized spent ionic liquid from an ionic liquid caustic wash zone, and a spent caustic stream from an acid gas scrubber zone; in a thermal oxidation system, comprising; thermally oxidizing the at least one of the acid ASO stream from the liquid acid alkylation process section, the acid gas stream from the liquid acid alkylation process section, the acid liquid stream from the liquid acid alkylation process section, the acid spent ionic liquid from the ionic liquid alkylation process section, the acid gas stream from the ionic liquid alkylation process section, the neutralized ASO stream from the caustic wash zone, and the spent caustic stream from the acid gas scrubber zone; or the acid liquid stream from the ionic liquid alkylation process section, the neutralized spent ionic liquid from the ionic liquid caustic wash zone, and the spent caustic stream from the acid gas scrubber zone, in a thermal oxidizing section forming flue gas consisting essentially of at least one of $H_2O$, $CO_2$, $N_2$, $O_2$, SOx, NOx, HCl, $Cl_2$, HF, $F_2$, $Na_2O$, $Na_2SO_3$, $Na_2SO_4$, $Na_2CO_3$, NaCl, NaF, $CaF_2$, CaO, $CaSO_3$, $CaSO_4$, $CaCO_3$, $CaCl_2$, $K_2O$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO; optionally recovering waste heat from the flue gas in a waste heat recovery section; removing at least one of SOx, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO from the flue gas in a contaminant removal section to form a decontaminated outlet flue gas consisting essentially of at least one of $H_2O$, $CO_2$, $N_2$, $O_2$, and NOx, wherein removing the at least one of SOx, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO from the flue gas comprises quenching the flue gas in a quench section to form quenched flue gas after recovering the waste heat; and contacting a caustic solution with the quenched flue gas in a contaminant scrubbing section to form the decontaminated outlet flue gas and a liquid stream comprising at least one of $H_2O$, NaCl, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO; or reacting the flue gas with a reactant in a contaminant reaction section to form a reaction section flue gas consisting essentially of at least one of $H_2O$, $CO_2$, $N_2$, $O_2$, $Na_2SO_4$, $Na_2CO_3$, NaCl, NaF, $CaF_2$, $CaSO_4$, $CaCO_3$, $CaCl_2$, $K_2SO_4$, $K_2CO_3$, KCl, KF, $Al_2O_3$, NiO, FeO, $FeO_2$, $Fe_2O_3$, $Fe_3O_4$, and CuO wherein the reactant comprises at least one of $NaHCO_3$, $NaHCO_3.Na_2CO_3.2(H_2O)$, $CaCO_3$, and $Ca(OH)_2$; and filtering the reaction section flue gas in a filtration section to remove at least one of $Na_2SO_4$, $Na_2CO_3$, NaCl, NaF, $CaF_2$, $CaSO_4$, $CaCO_3$, $CaCl_2$, $K_2SO_4$, $K_2CO_3$, KCl, KF, $Al_2O_3$, NiO, FeO, $FeO_2$, $Fe_2O_3$, $Fe_3O_4$, and CuO to form the decontaminated outlet flue gas; and optionally removing NOx from the decontaminated outlet flue gas in an NOx removal section to form a de-NOx outlet flue gas consisting essentially of at least one of $H_2O$, $CO_2$, $N_2$, and $O_2$. An embodiment of the invention is one, any or all of prior embodiments in this paragraph up through the first embodiment in this paragraph wherein the liquid acid alkylation process section comprises an HF alkylation process section or an $H_2SO_4$ alkylation process section. An embodiment of the invention is one, any or all of prior embodiments in this paragraph up through the first embodiment in this paragraph wherein the liquid acid alkylation process section comprises an HF alkylation process section, further comprising alkylating a $C_{3-4}$ olefin stream comprising propylene and butene and an isobutane stream comprising isobutane in the HF alkylation process section in the presence of an acid catalyst comprising HF to produce a reaction mixture comprising alkylate, unreacted propylene, unreacted normal butene, HF catalyst, and spent HF catalyst; separating the reaction mixture into an alkylate stream, an HF catalyst stream, the acid ASO stream comprising spent HF catalyst, the acid gas stream, the acid liquid stream, and a stream comprising at least one of the unreacted propylene and the unreacted normal butene; thermally oxidizing at least one of the acid ASO stream, the acid gas stream, and the acid liquid stream. An embodiment of the invention is one, any or all of prior embodiments in this paragraph up through the first embodiment in this paragraph further comprising neutralizing at least one of the acid ASO stream, the acid gas stream, the acid liquid stream with caustic forming at least one of the neutralized ASO stream, a neutralized gas stream, a neutralized liquid stream, and a spent caustic stream; thermally oxidizing at least one of the neutralized ASO stream, the neutralized gas stream, the neutralized liquid stream, and the spent caustic stream. An embodiment of the invention is one, any or all of prior embodiments in this paragraph up through the first embodiment in this paragraph further comprising introducing at least one of the neutralized ASO stream into a neutralized ASO surge tank before thermally oxidizing the neutralized ASO stream and introducing the neutralized liquid stream into a neutralized liquid surge tank before thermally oxidizing the neutralized liquid stream. An embodiment of the invention is one, any or all of prior embodiments in this paragraph up through the first embodiment in this paragraph further comprising introducing at least one of the acid ASO stream into an acid ASO surge tank before thermally oxidizing the acid ASO stream and introducing the acid liquid stream into an acid liquid surge tank before thermally oxidizing the acid liquid stream. An embodiment of the invention is one, any or all of prior embodiments in this paragraph up through the first embodiment in this paragraph wherein the alkylation process section comprises an $H_2SO_4$ alkylation process section, further comprising alkylating a $C_{3-4}$ olefin stream comprising propylene and butene and an isobutane stream comprising isobutane in the $H_2SO_4$ alkylation process section in the presence of an acid catalyst comprising $H_2SO_4$ to produce a reaction mixture comprising alkylate, unreacted propylene, unreacted normal butene, $H_2SO_4$ catalyst, and spent $H_2SO_4$ catalyst; separating the reaction mixture into an alkylate stream, an $H_2SO_4$ catalyst stream, the acid ASO stream comprising spent $H_2SO_4$ catalyst, the acid gas stream, the acid liquid stream, and a stream comprising at least one of the unreacted propylene and the unreacted normal butene; thermally oxidizing at least one of the acid ASO stream, the acid gas stream, and the acid liquid stream. An embodiment of the invention is one, any or all of prior embodiments in this paragraph up through the first embodiment in this paragraph further comprising neutralizing at least one of the acid ASO stream, the acid gas stream, the acid liquid stream with caustic forming at least one of the neutralized ASO stream, the neutralized gas stream, the neutralized liquid stream, and a spent caustic stream; thermally oxidizing at least one of the neutralized ASO stream, the neutralized gas stream, the neutralized liquid stream, and the spent caustic stream. An embodiment of the invention is one, any or all of prior embodiments in this paragraph up through the first embodiment in this paragraph further comprising introducing at least one of the neutralized ASO stream into a neutralized ASO surge tank before thermally oxidizing the neutralized ASO stream and introducing the neutralized liquid stream into a neutralized liquid surge tank before thermally oxidizing the neutralized liquid stream. An embodiment of the invention is one, any or all of prior embodiments in this paragraph up through the first embodiment in this paragraph further comprising introducing at least one the acid ASO stream into an acid ASO surge tank before thermally oxidizing the acid ASO stream, and introducing the acid liquid stream into an acid liquid surge tank before thermally oxidizing the acid liquid stream. An embodiment of the invention is one, any or all of prior embodiments in this paragraph up through the first embodiment in this paragraph wherein the ionic liquid alkylation process section is present, further comprising alkylating a $C_{3-4}$ olefin stream comprising propylene and butene and an isobutene stream comprising isobutane in the ionic liquid alkylation process section in the presence of an acid catalyst comprising an ionic liquid to produce a reaction mixture comprising alkylate, unreacted propylene, unreacted normal butene, ionic liquid catalyst, and spent ionic liquid catalyst; separating the reaction mixture into an alkylate stream, an ionic liquid catalyst stream, the acid spent ionic liquid stream comprising spent ionic liquid catalyst, the acid gas stream, the acid liquid stream, and a stream comprising at least one of the unreacted propylene and the unreacted normal butene; thermally oxidizing at least one of the acid spent ionic liquid stream, the acid gas stream, and the acid liquid stream. An embodiment of the invention is one, any or all of prior embodiments in this paragraph up through the first embodiment in this paragraph further comprising neutralizing at least one of the acid spent ionic liquid stream, the acid gas stream, and the acid liquid stream with caustic forming at least one of the neutralized spent ionic liquid stream, a neutralized gas stream, a neutralized liquid stream, and a spent caustic stream; thermally oxidizing at least one of the neutralized spent ionic liquid stream, the neutralized gas stream, the neutralized liquid stream, and the spent caustic stream. An embodiment of the invention is one, any or all of prior embodiments in this paragraph up through the first embodiment in this paragraph further comprising introducing at least one of the neutralized spent ionic liquid stream into an neutralized ionic liquid surge tank before thermally oxidizing the neutralized spent ionic liquid stream, and introducing the neutralized liquid stream into a neutralized liquid surge tank or both before thermally oxidizing the neutralized liquid stream. An embodiment of the invention is one, any or all of prior embodiments in this paragraph up through the first embodiment in this paragraph further comprising introducing at least one of the acid spent ionic liquid stream into an acid spent ionic liquid surge tank before thermally oxidizing the acid spent ionic liquid, and introducing the acid liquid stream to an acid liquid surge tank before thermally oxidizing the acid liquid stream. An embodiment of the invention is one, any or all of prior embodiments in this paragraph up through the first embodiment in this paragraph wherein the ionic liquid comprises a chloroaluminate ionic liquid.

A second embodiment of the invention is a process for treating off-gas and waste effluent streams in an alkylation complex comprising alkylating a $C_{3-4}$ olefin stream comprising propylene and butene and an isobutane stream comprising isobutene in an liquid acid alkylation process section or an ionic liquid alkylation process section in the presence of an acid catalyst to produce a reaction mixture comprising alkylate, unreacted propylene, unreacted normal butene, acid catalyst, and spent acid catalyst, wherein the acid catalyst comprises HF, $H_2SO_4$, or an ionic liquid; separating the reaction mixture into at least one of and alkylate stream, the acid ASO stream, an acid gas stream from the liquid acid alkylation process section, an acid liquid stream from the liquid and an acid alkylation process section; or an acid spent ionic liquid from an ionic liquid alkylation process section, an acid gas stream from the ionic liquid alkylation process section, an acid liquid stream from the ionic liquid alkylation process section, and a stream comprising at least one of the unreacted propylene and the unreacted normal butene; thermally oxidizing at least one of the acid ASO stream, the acid gas stream from the liquid acid alkylation process section, the acid liquid stream from the liquid acid alkylation process section, a neutralized ASO stream from a caustic wash zone, and a spent caustic stream from an acid gas scrubber zone; or the acid spent ionic liquid from an ionic liquid alkylation process section, the acid gas stream from the ionic liquid alkylation process section, the acid liquid stream from the ionic liquid alkylation process section, a neutralized spent ionic liquid from an ionic liquid caustic wash zone, and a spent caustic stream from an acid gas scrubber zone; in a thermal oxidation system, comprising; thermally oxidizing the at least one of the acid ASO stream from the liquid acid alkylation process section, the acid gas stream from the liquid acid alkylation process section, the acid liquid stream from the liquid acid alkylation process section, the acid spent ionic liquid from the ionic liquid alkylation process section, the acid gas stream from the ionic liquid alkylation process section, the neutralized ASO stream from the caustic wash zone, and the spent caustic stream from the acid gas scrubber zone; or the acid liquid stream from the ionic liquid alkylation process section, the neutralized spent ionic liquid from the ionic liquid caustic wash zone, and the spent caustic stream from the acid gas scrubber zone, in a thermal oxidizing section forming flue gas consisting essentially of at least one of $H_2O$, $CO_2$, $N_2$, $O_2$, SOx, NOx, HCl, $Cl_2$, HF, $F_2$, $Na_2O$, $Na_2SO_3$, $Na_2SO_4$, $Na_2CO_3$, NaCl, NaF, $CaF_2$, CaO, $CaSO_3$, $CaSO_4$, $CaCO_3$, $CaCl_2$, $K_2O$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO; optionally recovering waste heat from the flue gas in a waste heat recovery section; removing at least one of SOx, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO from the flue gas in a contaminant removal section to form a decontaminated outlet flue gas consisting essentially of at least one of $H_2O$, $CO_2$, $N_2$, $O_2$, and NOx, wherein removing the at least one of SOx, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO from the flue gas comprises quenching the flue gas in a quench section to form quenched flue gas after recovering the waste heat; and contacting a caustic solution with the quenched flue gas in a contaminant scrubbing section to form the decontaminated outlet flue gas and a liquid stream comprising at least one of $H_2O$, NaCl, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO; or reacting the flue gas with a reactant in a contaminant reaction section to form a reaction section flue gas consisting essentially of at least one of $H_2O$, $CO_2$, $N_2$, $O_2$, $Na_2SO_4$, $Na_2CO_3$, NaCl, NaF, $CaF_2$, $CaSO_4$, $CaCO_3$, $CaCl_2$, $K_2SO_4$, $K_2CO_3$, KCl, KF, $Al_2O_3$, NiO, FeO, $FeO_2$, $Fe_2O_3$, $Fe_3O_4$, and CuO wherein the reactant comprises at least one of $NaHCO_3$, $NaHCO_3.Na_2CO_3.2(H_2O)$, $CaCO_3$ and $Ca(OH)_2$; and filtering the reaction section flue gas in a filtration section to remove $Na_2SO_4$, $Na_2CO_3$, NaCl, NaF, $CaF_2$, $CaSO_4$, $CaCO_3$, $CaCl_2$, $K_2SO_4$, $K_2CO_3$, KCl, KF, $Al_2O_3$, NiO, FeO, $FeO_2$, $Fe_2O_3$, $Fe_3O_4$, and CuO to form the decontaminated outlet flue gas; and optionally removing NOx from the decontaminated outlet flue gas in an NOx removal section to form a de-NOx outlet flue gas consisting essentially of at least one of $H_2O$, $CO_2$, $N_2$, and $O_2$. An embodiment of the invention is one, any or all of prior embodiments in this paragraph up through the second embodiment in this paragraph further comprising neutralizing at least one of the acid ASO stream, the acid gas stream from the liquid acid alkylation process section, the acid liquid stream from the liquid acid alkylation process section, the acid spent ionic liquid stream, the acid gas stream from the ionic liquid alkylation process section, the acid liquid stream from the ionic liquid alkylation process section with caustic forming the neutralized ASO stream, a neutralized gas stream from the liquid acid alkylation process section, a neutralized liquid stream from the liquid acid alkylation process section, the neutralized spent ionic liquid stream, a neutralized gas stream from the ionic liquid alkylation process section, a neutralized liquid stream from the ionic liquid alkylation process section, and the spent caustic stream; thermally oxidizing at least one of the neutralized ASO stream, the neutralized liquid stream from the liquid acid alkylation process section the neutralized spent ionic liquid stream, the neutralized liquid stream from the ionic gas alkylation process section, the neutralized liquid stream from the ionic liquid alkylation process section, and the spent caustic stream. An embodiment of the invention is one, any or all of prior embodiments in this paragraph up through the second embodiment in this paragraph further comprising introducing at least one of the neutralized ASO stream into a neutralized ASO surge tank before thermally oxidizing the neutralized ASO stream, the neutralized liquid stream from the liquid acid alkylation process section into a neutralized liquid surge tank before thermally oxidizing the neutralized liquid stream, the neutralized spent ionic liquid stream into a neutralized spent ionic liquid surge tank before thermally oxidizing the neutralized spent ionic liquid stream, the neutralized liquid stream from the ionic gas alkylation process section into a neutralized liquid surge tank before thermally oxidizing the neutralized liquid stream, and the spent caustic stream into a spent caustic surge tank before thermally oxidizing the spent caustic stream. An embodiment of the invention is one, any or all of prior embodiments in this paragraph up through the second embodiment in this paragraph wherein the ionic liquid comprises a chloroaluminate ionic liquid.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for treating off-gas and waste effluent streams in an alkylation complex comprising:

thermally oxidizing at least one of: an acid soluble oil (acid ASO) stream from a liquid acid alkylation process section of an HF alkylation process or an $H_2SO_4$ alkylation process, an acid gas stream from the liquid acid alkylation process section, an acid liquid stream from the liquid acid alkylation process section, a neutralized ASO stream from a caustic wash zone, and a spent caustic stream from an acid gas scrubber zone of the HF alkylation process or the $H_2SO_4$ alkylation process; or an acid spent ionic liquid from an ionic liquid alkylation process section of an ionic liquid alkylation process, an acid gas stream from the ionic liquid alkylation process section, an acid liquid stream from the ionic liquid alkylation process section, a neutralized spent ionic liquid from an ionic liquid caustic wash zone, and a spent caustic stream from an acid gas scrubber zone of the ionic liquid alkylation process; in a thermal oxidation section of a thermal oxidation system and thereby forming flue gas consisting essentially of at least one of $H_2O$, $CO_2$, $N_2$, $O_2$, SOx, NOx, HCl, $Cl_2$, HF, $F_2$, $Na_2O$, $Na_2SO_3$, $Na_2SO_4$, $Na_2CO_3$, NaCl, NaF, $CaF_2$, CaO, $CaSO_3$, $CaSO_4$, $CaCO_3$, $CaCl_2$, $K_2O$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO;

optionally recovering waste heat from the flue gas in a waste heat recovery section of the thermal oxidizing system;

removing at least one of SOx, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO from the flue gas in a contaminant removal section of the thermal oxidizing system to form a decontaminated outlet flue gas consisting essentially of at least one of $H_2O$, $CO_2$, $N_2$, $O_2$, and NOx, wherein removing the at least one of SOx, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO from the flue gas comprises:

quenching the flue gas from the thermal oxidation section or from the waste heat recovery section in a quench section of the thermal oxidizing system to form quenched flue gas; and contacting a caustic solution with the quenched flue gas in a contaminant scrubbing section of the thermal oxidizing system to form the decontaminated outlet flue gas and a liquid stream comprising at least one of $H_2O$, NaCl, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO;

or reacting the flue gas with a reactant in a contaminant reaction section of the thermal oxidizing system to form a reaction section flue gas consisting essentially of at least one of $H_2O$, $CO_2$, $N_2$, $O_2$, $Na_2SO_4$, $Na_2CO_3$, NaCl, NaF, $CaF_2$, $CaSO_4$, $CaCO_3$, $CaCl_2$, $K_2SO_4$, $K_2CO_3$, KCl, KF, $Al_2O_3$, NiO, FeO, $FeO_2$, $Fe_2O_3$, $Fe_3O_4$, and CuO wherein the reactant comprises at least one of $NaHCO_3$, $NaHCO_3 \cdot Na_2CO_3 \cdot 2(H_2O)$, $CaCO_3$ and $Ca(OH)_2$; and filtering the reaction section flue gas in a filtration section of the thermal oxidizing system to remove at least one of $Na_2SO_4$, $Na_2CO_3$, NaCl, NaF, $CaF_2$, $CaSO_4$, $CaCO_3$, $CaCl_2$, $K_2SO_4$, $K_2CO_3$, KCl, KF, $Al_2O_3$, NiO, FeO, $FeO_2$, $Fe_2O_3$, $Fe_3O_4$, and CuO to form the decontaminated outlet flue gas; and optionally removing NOx from the decontaminated outlet flue gas in an NOx removal section of the thermal oxidizing system to form a de-NOx outlet flue gas consisting essentially of at least one of $H_2O$, $CO_2$, $N_2$, and $O_2$.

2. The process of claim 1 wherein the liquid acid alkylation process section comprises an HF alkylation process section or an $H_2SO_4$ alkylation process section.

3. The process of claim 1 wherein the liquid acid alkylation process section comprises an HF alkylation process section, further comprising:

alkylating a $C_{3-4}$ olefin stream comprising propylene and butene and an isobutane stream comprising isobutane in the HF alkylation process section in the presence of an acid catalyst comprising HF to produce a reaction mixture comprising alkylate, unreacted propylene, unreacted normal butene, HF catalyst, and spent HF catalyst;

separating the reaction mixture into an alkylate stream, an HF catalyst stream, the acid ASO stream comprising spent HF catalyst, the acid gas stream, the acid liquid stream, and a stream comprising at least one of the unreacted propylene and the unreacted normal butene; and thermally oxidizing at least one of the acid ASO stream, the acid gas stream, and the acid liquid stream.

4. The process of claim 3 further comprising:

neutralizing at least one of the acid ASO stream, the acid gas stream, the acid liquid stream with caustic forming at least one of the neutralized ASO stream, a neutralized gas stream, a neutralized liquid stream, and a spent caustic stream; and thermally oxidizing at least one of the neutralized ASO stream, the neutralized gas stream, the neutralized liquid stream, and the spent caustic stream.

5. The process of claim 4 further comprising:
at least one of introducing the neutralized ASO stream into a neutralized ASO surge tank before thermally oxidizing the neutralized ASO stream and introducing the neutralized liquid stream into a neutralized liquid surge tank before thermally oxidizing the neutralized liquid stream.

6. The process of claim 3 further comprising:
at least one of introducing the acid ASO stream into an acid ASO surge tank before thermally oxidizing the acid ASO stream and introducing the acid liquid stream into an acid liquid surge tank before thermally oxidizing the acid liquid stream.

7. The process of claim 1 wherein the alkylation process section comprises an $H_2SO_4$ alkylation process section, further comprising:
alkylating a $C_{3-4}$ olefin stream comprising propylene and butene and an isobutane stream comprising isobutane in the $H_2SO_4$ alkylation process section in the presence of an acid catalyst comprising $H_2SO_4$ to produce a reaction mixture comprising alkylate, unreacted propylene, unreacted normal butene, $H_2SO_4$ catalyst, and spent $H_2SO_4$ catalyst;
separating the reaction mixture into an alkylate stream, an $H_2SO_4$ catalyst stream, the acid ASO stream comprising spent $H_2SO_4$ catalyst, the acid gas stream, the acid liquid stream, and a stream comprising at least one of the unreacted propylene and the unreacted normal butene; and
thermally oxidizing at least one of the acid ASO stream, the acid gas stream, and the acid liquid stream.

8. The process of claim 7 further comprising:
neutralizing at least one of the acid ASO stream, the acid gas stream, the acid liquid stream with caustic forming at least one of the neutralized ASO stream, the neutralized gas stream, the neutralized liquid stream, and a spent caustic stream; and
thermally oxidizing at least one of the neutralized ASO stream, the neutralized gas stream, the neutralized liquid stream, and the spent caustic stream.

9. The process of claim 8 further comprising:
at least one of introducing the neutralized ASO stream into a neutralized ASO surge tank before thermally oxidizing the neutralized ASO stream and introducing the neutralized liquid stream into a neutralized liquid surge tank before thermally oxidizing the neutralized liquid stream.

10. The process of claim 7 further comprising:
at least one of introducing the acid ASO stream into an acid ASO surge tank before thermally oxidizing the acid ASO stream, and introducing the acid liquid stream into an acid liquid surge tank before thermally oxidizing the acid liquid stream.

11. The process of claim 1 wherein the ionic liquid alkylation process section is present, further comprising:
alkylating a $C_{3-4}$ olefin stream comprising propylene and butene and an isobutane stream comprising isobutane in the ionic liquid alkylation process section in the presence of an acid catalyst comprising an ionic liquid to produce a reaction mixture comprising alkylate, unreacted propylene, unreacted normal butene, ionic liquid catalyst, and spent ionic liquid catalyst;
separating the reaction mixture into an alkylate stream, an ionic liquid catalyst stream, the acid spent ionic liquid stream comprising spent ionic liquid catalyst, the acid gas stream, the acid liquid stream, and a stream comprising at least one of the unreacted propylene and the unreacted normal butene; and
thermally oxidizing at least one of the acid spent ionic liquid stream, the acid gas stream, and the acid liquid stream.

12. The process of claim 11 further comprising:
neutralizing at least one of the acid spent ionic liquid stream, the acid gas stream, and the acid liquid stream with caustic forming at least one of the neutralized spent ionic liquid stream, a neutralized gas stream, a neutralized liquid stream, and a spent caustic stream; and
thermally oxidizing at least one of the neutralized spent ionic liquid stream, the neutralized gas stream, the neutralized liquid stream, and the spent caustic stream.

13. The process of claim 12 further comprising:
at least one of introducing the neutralized spent ionic liquid stream into an neutralized ionic liquid surge tank before thermally oxidizing the neutralized spent ionic liquid stream, and introducing the neutralized liquid stream into a neutralized liquid surge tank or both before thermally oxidizing the neutralized liquid stream.

14. The process of claim 11 further comprising:
at least one of introducing the acid spent ionic liquid stream into an acid spent ionic liquid surge tank before thermally oxidizing the acid spent ionic liquid, and introducing the acid liquid stream to an acid liquid surge tank before thermally oxidizing the acid liquid stream.

15. The process of claim 11 wherein the ionic liquid comprises a chloroaluminate ionic liquid.

16. The process of claim 1 further comprising:
quenching the reaction section flue gas before filtering the reaction section flue gas.

17. A process for treating off-gas and waste effluent streams in an alkylation complex comprising:
alkylating a $C_{3-4}$ olefin stream comprising propylene and butene and an isobutane stream comprising isobutene in an liquid acid alkylation process section or an ionic liquid alkylation process section in the presence of an acid catalyst to produce a reaction mixture comprising alkylate, unreacted propylene, unreacted normal butene, acid catalyst, and spent acid catalyst, wherein the acid catalyst comprises HF, $H_2SO_4$, or an ionic liquid;
separating the reaction mixture into at least one of: an alkylate stream, an acid ASO stream, an acid gas stream from the liquid acid alkylation process section, an acid liquid stream from the liquid and an acid alkylation process section; or an acid spent ionic liquid from an ionic liquid alkylation process section, an acid gas stream from the ionic liquid alkylation process section, an acid liquid stream from the ionic liquid alkylation process section, and a stream comprising at least one of the unreacted propylene and the unreacted normal butene;
thermally oxidizing at least one of: an acid soluble oil (acid ASO) stream from a liquid acid alkylation process section of an HF alkylation process or an $H_2SO_4$ alkylation process, an acid gas stream from the liquid acid alkylation process section, an acid liquid stream from the liquid acid alkylation process section, a neutralized ASO stream from a caustic wash zone, and a spent caustic stream from an acid gas scrubber zone of the HF alkylation process or the $H_2SO_4$ alkylation process; or an acid spent ionic liquid from an ionic liquid alkylation process section of an ionic liquid alkylation process, an acid gas stream from the ionic liquid alkylation process section, an acid liquid stream from the ionic liquid alkylation process section, a neutralized spent ionic liquid from an ionic liquid caustic wash zone, and a spent caustic stream from an acid gas scrubber zone of the ionic liquid alkylation process; in a thermal oxidation section of a thermal oxidation system and thereby forming flue gas consisting essentially of at least one of $H_2O$, $CO_2$, $N_2$, $O_2$, SOx, NOx, HCl, $Cl_2$, HF, $F_2$, $Na_2O$, $Na_2SO_3$, $Na_2SO_4$, $Na_2CO_3$, NaCl, NaF, $CaF_2$, CaO, $CaSO_3$, $CaSO_4$, $CaCO_3$, $CaCl_2$, $K_2O$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO;

optionally recovering waste heat from the flue gas in a waste heat recovery section of the thermal oxidizing system;

removing at least one of SOx, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO from the flue gas in a contaminant removal section of the thermal oxidizing system to form a decontaminated outlet flue gas consisting essentially of at least one of $H_2O$, $CO_2$, $N_2$, $O_2$, and NOx, wherein removing the at least one of SOx, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO from the flue gas comprises:

quenching the flue gas from the thermal oxidation section or from the waste heat recovery section in a quench section to form quenched flue gas; and contacting a caustic solution with the quenched flue gas in a contaminant scrubbing section of the thermal oxidizing system to form the decontaminated outlet flue gas and a liquid stream comprising at least one of $H_2O$, NaCl, HCl, $Cl_2$, HF, $F_2$, $Na_2SO_3$, $Na_2SO_4$, $Na_2CO_3$, NaCl, NaF, $CaF_2$, $CaSO_3$, $CaSO_4$, $CaCO_3$, $CaCl_2$, $K_2SO_3$, $K_2SO_4$, $K_2CO_3$, KCl, KF, $Al_2O_3$, NiO, FeO, $FeO_2$, $Fe_2O_3$, $Fe_3O_4$, and CuO;

or reacting the flue gas with a reactant in a contaminant reaction section of the thermal oxidizing system to form a reaction section flue gas consisting essentially of at least one of $H_2O$, $CO_2$, $N_2$, $O_2$, $Na_2SO_4$, $Na_2CO_3$, NaCl, NaF, $CaF_2$, $CaSO_4$, $CaCO_3$, $CaCl_2$, $K_2SO_4$, $K_2CO_3$, KCl, KF, $Al_2O_3$, NiO, FeO, $FeO_2$, $Fe_2O_3$, $Fe_3O_4$, and CuO wherein the reactant comprises at least one of $NaHCO_3$, $NaHCO_3.Na_2CO_3.2(H_2O)$, $CaCO_3$ and $Ca(OH)_2$; and filtering the reaction section flue gas in a filtration section of the thermal oxidizing system to remove $Na_2SO_4$, $Na_2CO_3$, NaCl, NaF, $CaF_2$, $CaSO_4$, $CaCO_3$, $CaCl_2$, $K_2SO_4$, $K_2CO_3$, KCl, KF, $Al_2O_3$, NiO, FeO, $FeO_2$, $Fe_2O_3$, $Fe_3O_4$, and CuO to form the decontaminated outlet flue gas; and optionally removing NOx from the decontaminated outlet flue gas in an NOx removal section of the thermal oxidizing system to form a de-NOx outlet flue gas consisting essentially of at least one of $H_2O$, $CO_2$, $N_2$, and $O_2$.

18. The process of claim 17 further comprising:

neutralizing at least one of the acid ASO stream, the acid gas stream from the liquid acid alkylation process section, the acid liquid stream from the liquid acid alkylation process section, the acid spent ionic liquid stream, the acid gas stream from the ionic liquid alkylation process section, the acid liquid stream from the ionic liquid alkylation process section with caustic forming the neutralized ASO stream, a neutralized gas stream from the liquid acid alkylation process section, a neutralized liquid stream from the liquid acid alkylation process section, the neutralized spent ionic liquid stream, a neutralized gas stream from the ionic liquid alkylation process section, a neutralized liquid stream from the ionic liquid alkylation process section, and the spent caustic stream; and thermally oxidizing at least one of the neutralized ASO stream, the neutralized liquid stream from the liquid acid alkylation process section the neutralized spent ionic liquid stream, the neutralized liquid stream from the ionic gas alkylation process section, the neutralized liquid stream from the ionic liquid alkylation process section, and the spent caustic stream.

19. The process of claim 18 further comprising:

introducing at least one of: the neutralized ASO stream into a neutralized ASO surge tank before thermally oxidizing the neutralized ASO stream, the neutralized liquid stream from the liquid acid alkylation process section into a neutralized liquid surge tank before thermally oxidizing the neutralized liquid stream, the neutralized spent ionic liquid stream into a neutralized spent ionic liquid surge tank before thermally oxidizing the neutralized spent ionic liquid stream, the neutralized liquid stream from the ionic gas alkylation process section into a neutralized liquid surge tank before thermally oxidizing the neutralized liquid stream, and the spent caustic stream into a spent caustic surge tank before thermally oxidizing the spent caustic stream.

20. The process of claim 17 wherein the ionic liquid comprises a chloroaluminate ionic liquid.

* * * * *